United States Patent
Kaneko et al.

(10) Patent No.: US 10,633,674 B2
(45) Date of Patent: Apr. 28, 2020

(54) MAMMALIAN GENE MODIFICATION METHOD USING ELECTROPORATION

(71) Applicant: NEPA GENE CO., LTD., Ichikawa-shi (JP)

(72) Inventors: Takehito Kaneko, Kyoto (JP); Tomoji Mashimo, Kyoto (JP); Yasuhiko Hayakawa, Ichikawa (JP); Kiyoshi Hayakawa, Ichikawa (JP)

(73) Assignee: NEPA GENE CO., LTD., Ichikawa-shi (JP)

( * ) Notice: Subject to any disclaimer, the term of this patent is extended or adjusted under 35 U.S.C. 154(b) by 337 days.

(21) Appl. No.: 15/025,365

(22) PCT Filed: May 27, 2014

(86) PCT No.: PCT/JP2014/063910
§ 371 (c)(1),
(2) Date: Mar. 28, 2016

(87) PCT Pub. No.: WO2015/049897
PCT Pub. Date: Apr. 9, 2015

(65) Prior Publication Data
US 2016/0215297 A1 Jul. 28, 2016

(30) Foreign Application Priority Data
Oct. 4, 2013 (JP) ................................ 2013-209184

(51) Int. Cl.
| | | |
|---|---|---|
| *C12N 15/85* | (2006.01) | |
| *C12N 15/90* | (2006.01) | |
| *C12N 15/87* | (2006.01) | |
| *C07K 14/715* | (2006.01) | |
| *A01K 67/027* | (2006.01) | |
| *C12N 9/22* | (2006.01) | |
| *C12N 13/00* | (2006.01) | |

(52) U.S. Cl.
CPC ...... *C12N 15/8509* (2013.01); *A01K 67/0276* (2013.01); *C07K 14/7155* (2013.01); *C12N 9/22* (2013.01); *C12N 13/00* (2013.01); *C12N 15/87* (2013.01); *C12N 15/907* (2013.01); *A01K 2227/105* (2013.01); *A01K 2267/0381* (2013.01)

(58) Field of Classification Search
CPC .... C12N 15/8509; C12N 13/00; C12N 15/87; C12N 15/907; C12N 9/22; A01K 67/0276; A01K 2227/105; A01K 2267/0381; C07K 14/7155
See application file for complete search history.

(56) References Cited

FOREIGN PATENT DOCUMENTS

| CN | 102 329 819 B | 12/2012 |
|---|---|---|
| WO | WO 2013/139994 A1 | 9/2013 |

OTHER PUBLICATIONS

Sato et al. "Nucleic acids delivery methods for genome editing in zygotes and embryos: the old, the new, and the old-new." Biol Direct. Mar. 31, 2016;11(1):16 (Year: 2016).*
Grabarek et al. "Efficient delivery of dsRNA into zona-enclosed mouse oocytes and preimplantation embryos by electroporation." Genesis. Apr. 2002;32(4):269-76. (Year: 2002).*
Kaneko et al. "Simple knockout by electroporation of engineered endonucleases into intact rat embryos." Sci Rep. Oct. 1, 2014;4: 6382. (Year: 2014).*
Peng et al. "Efficient Delivery of DNA and Morpholinos into Mouse Preimplantation Embryos by Electroporation." PLoS One. 2012; 7(8): e43748. (Year: 2012).*
Phillips D.M. (1991) Structure and Function of the Zona Pellucidan: Familiari G., Makabe S., Motta P.M. (eds) Ultrastructure of the Ovary. Electron Microscopy in Biology and Medicine (Current Topics in Ultrastructural Research), vol. 9. Springer, Boston, MA (Year : 1991).*
Hirata et al. "Genome mutation after introduction of the gene editing by electroporation of Cas9 protein (GEEP) system in matured oocytes and putative zygotes." In Vitro Cell Dev Biol Anim. Apr. 2019;55(4):237-242 (Year: 2019).*
Tanihara et al. "Somatic cell reprogramming-free generation of genetically modified pigs." Sci Adv. Sep. 14, 2016;2(9):e1600803. (Year: 2016).*
Nishio et al. "Effects of voltage strength during electroporation on the development and quality of in vitro-produced porcine embryos." Reprod Domest Anim. Apr. 2018;53(2):313-318. (Year: 2018).*
Takahashi et al. "GONAD: Genome-editing via Oviductal Nucleic Acids Delivery system: a novel microinjection independent genome engineering method in mice." Sci Rep. Jun. 22, 2015;5:11406 (Year: 2015).*
Remy et al. "Generation of gene-edited rats by delivery of CRISPR/ Cas9 protein and donor DNA into intact zygotes using electroporation." Sci Rep. Nov. 29, 2017;7(1):16554. (Year: 2017).*
Tomoji Mashimo, "New Genetic Modification Technology, "Zinc Finger Nuclease (ZFN)", Several advantages including production of knockout animal in short period of time", Japan Society for Bioscience, Biotechnology, and Agrochemistry, vol. 49, No. 4. Total 5 Pages. (Apr. 1, 2011) (with partial English translation).

(Continued)

*Primary Examiner* — Titilayo Moloye
(74) *Attorney, Agent, or Firm* — Oblon, McClelland, Maier & Neustadt, L.L.P.

(57) ABSTRACT

An object is to develop a technology enabling utilization, by only an extremely simple technique, of a technology which is widely applicable to mammals without requiring the utilization of an ES cell, and which involves modifying a certain gene by targeting a certain sequence on a genome (genome editing technology based on ZFN or the like). Provided is a technology for efficiently modifying an arbitrary target gene of a mammal, by immersing a pronuclear stage mammalian zygote with an intact zona pellucida into a solution containing a pair of molecules of mRNA having a certain sequence, and performing electroporation treatment through application of multiple square-wave pulses in three steps with the total electric energy of a first electric pulse adjusted within a predetermined range.

9 Claims, 4 Drawing Sheets

Specification includes a Sequence Listing.

(56) References Cited

OTHER PUBLICATIONS

Tomoji Mashimo, et al., "Zinc Finger Nuclease (ZFN)", Cell Technology, vol. 31, No. 3, Total 8 Pages, (Feb. 22, 2012) (with partial English translation).

Tomoji Mashimo, et al., "New Development of Genetic Modification Technology in Rats", Cell Technology, vol. 32, No. 5, Total 8 Pages, (Apr. 22, 2013) (with partial English translation).

Ryan M. Walsh, et al., "A variant CRISPR-Cas9 system adds versatility to genome engineering", PNAS, vol. 110, No. 39, pp. 15514-15515, (Sep. 24, 2013).

Joanna B. Grabarek, et al., "Efficient Delivery of dsRNA into Zona-Enclosed Mouse Oocytes and Preimplantation Embryos by Electroporation", Genesis, vol. 32, pp. 269-276, (2002).

Hui Peng, et al., "Efficient Delivery of DNA and Morpholinos into Mouse Preimplantation Embryos by Electroporation", PLOS ONE, vol. 7, No. 8, pp. 1-13, (Aug. 2012).

Kosuke Shimogawara, et al., "High-Efficiency Transformation of *Chlamydomonas reinhardtii* by Electroporation", Genetics, vol. 148, pp. 1821-1828, (Apr. 1998).

S. I. Sukharev, et al., "Electroporation and electrophoretic DNA transfer into cells, The effect of DNA interaction with electropores", Biophysical Journal, vol. 63, pp. 1320-1327, (Nov. 1992).

International Search Report dated Sep. 9, 2014 in PCT/JP14/063910 Filed May 27, 2014.

Kaneko, Takehito et al., "Simple knockout by electroporation of engineered endonucleases into intact rat embryos", Scientific Reports, vol. 4, Oct. 2014, XP002768158.

\* cited by examiner 21    22

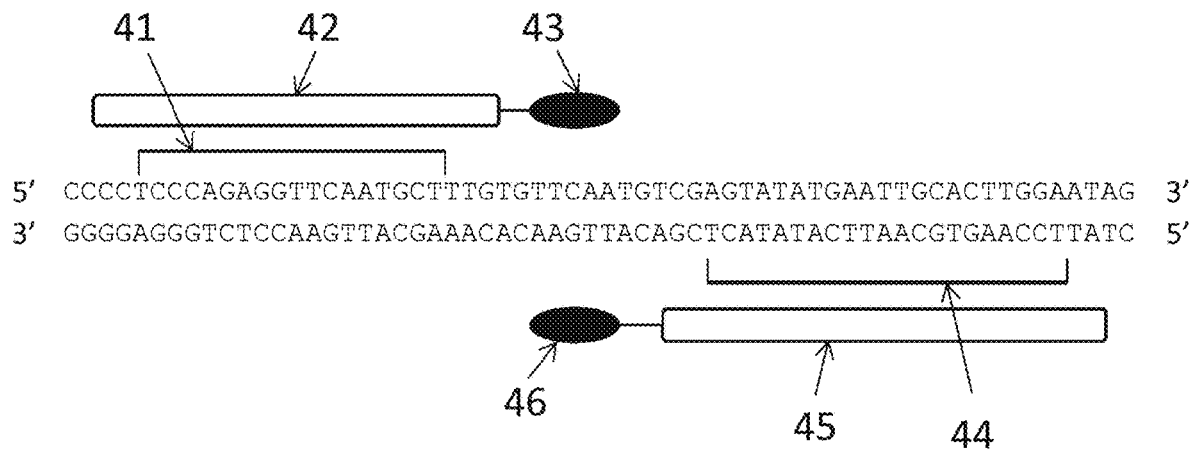
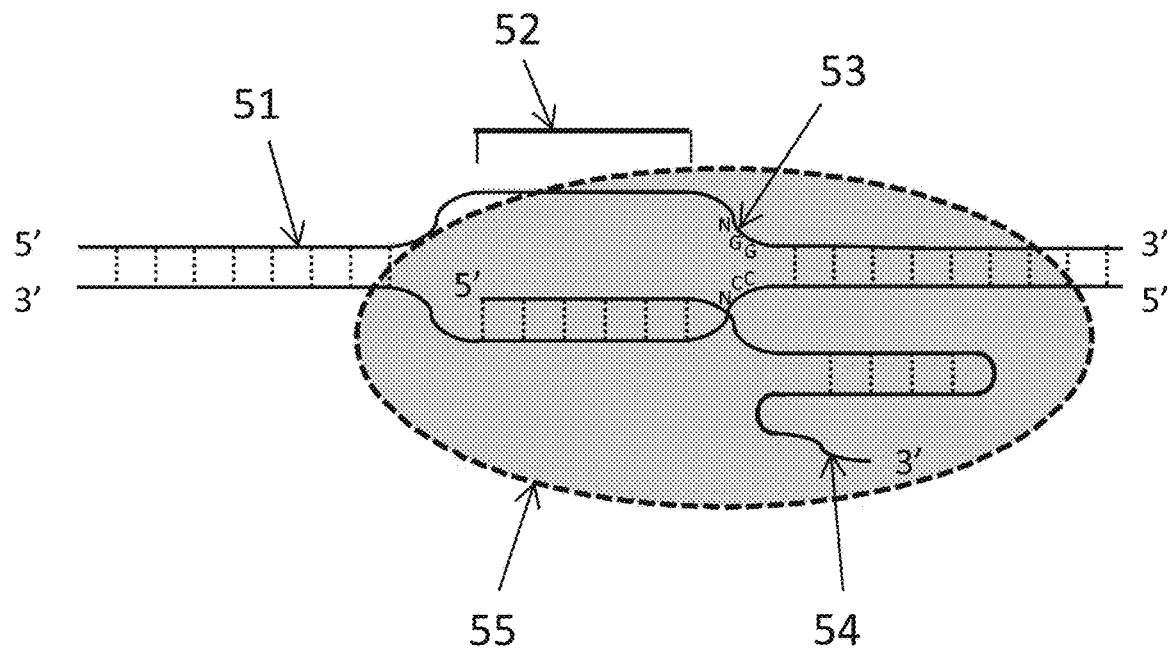

MAMMALIAN GENE MODIFICATION METHOD USING ELECTROPORATION

TECHNICAL FIELD

The present invention relates to a technology for efficiently modifying an arbitrary target gene of a mammal, by immersing a pronuclear-stage mammalian zygote with an intact zona pellucida into a solution containing a certain RNA molecule, and performing electroporation treatment through application of multiple square-wave pulses in three steps with total electric energy of a first electric pulse adjusted within a predetermined range.

BACKGROUND ART

Hitherto, it has been necessary to use an ES cell in order to perform gene modification of a mammal, and hence it has been extremely difficult to create a genetically modified individual except for some animals, such as mice, for which ES cell lines can be utilized. In recent years, however, a new gene modification technology involving utilizing, for example, a zinc finger nuclease (ZFN), TALEN, or CRISPR has emerged to enable genome editing in a mammal to be easily performed through only embryo manipulation without any use of an ES cell (see, for example, Non Patent Literatures 1 to 4).

The technology involving utilizing ZFN or the like is a breakthrough technology which uses a certain sequence on a genome as a target and enables disruption or homologous recombination of a certain gene through an action of a nuclease. In addition, this technology enables gene modification of a target sequence (genome editing) to be easily performed even for any animal for which there is no established ES cell system.

However, utilization of the genome editing technology based on ZFN or the like requires an operation of transferring a nucleic acid into a zygote. The nucleic acid transfer operation is generally performed by a microinjection method (microinjection), which requires a special device (micromanipulator). That is, a problem in cost has been pointed out in the genome editing technology based on ZFN or the like performing by the related-art method.

In addition, a technically skilled person is required for performing the microinjection method, and a problem of low reproducibility depending on experimenters has been pointed out.

As described above, utilization of the genome editing technology based on ZFN or the like for a mammal involves cost and technical problems. Accordingly, there is a demand for a technology which can be readily employed by anyone and can realize genome editing in a mammal with high efficiency.

CITATION LIST

Non Patent Literature

[NPL 1] Tomoji Mashimo: New Gene Modification Technology "Zinc Finger Nuclease (ZFN)": KAGAKU TO SEIBUTSU, edited by Japan Society for Bioscience, Biotechnology, and Agrochemistry, p 220-222 (2011)
[NPL 2] Tomoji Mashimo and Tadao Serikawa: Zinc Finger Nuclease (ZFN): Cell Technology vol. 31 (3) p 296-301 (2012)
[NPL 3] Genome Editing Revolution (supervisors: Takashi Yamamoto and Sumihare Noji): Cell Technology vol. 32 (5) (2013)
[NPL 4] Ryan M. Walsh and Konrad Hochedlinger, PNAS, vol. 110, no. 39, 15514-15515 (2013)

SUMMARY OF INVENTION

Technical Problem

An object of the present invention is to develop a technology enabling utilization, by only an extremely simple technique, of a technology which is widely applicable to mammals without requiring the utilization of an ES cell, and which involves modifying a certain gene by targeting a certain sequence on a genome (genome editing technology based on ZFN or the like).

Another object of the present invention is to enable the creation of a genetically modified individual of a mammal with high efficiency and good reproducibility without being limited to certain species of mammals.

Solution to Problem

The inventors of the present invention have made extensive investigations in order to attain the above-mentioned objects, and as a result, have found that a desired mammalian gene serving as a target can be efficiently modified by: immersing a pronuclear-stage mammalian zygote with an intact zona pellucida into a solution containing a certain RNA molecule; and then performing electroporation treatment involving applying a square-wave electric pulse (first electric pulse) with a high voltage for a short period of time under the condition that its total electric energy falls within a predetermined range, then applying a square-wave electric pulse (second electric pulse) with a low voltage for a long period of time two or more times, and then applying a square-wave electric pulse (third electric pulse) which is opposite in polarity to the second electric pulse, with a low voltage for a long period of time, two or more times (multiple square-wave pulses in three steps: see FIG. 1 and FIG. 2).

In particular, the inventors of the present invention have found that the following technical features are particularly important among those conditions: "using, as the zygote, a zygote of a mammal in a pronuclear stage"; "using, as the zygote, a zygote in a state of having a zona pellucida"; "using, as a nucleic acid molecular species, an RNA molecule having a certain sequence"; and "applying, as electric conditions for the electroporation, multiple square-wave pulses in three steps under electric pulse conditions within predetermined conditions."

The inventors of the present invention have also found that this technology is a technology widely applicable to mammals in general without being limited to certain species of mammals.

It should be noted that, in the related art, there is no report of an example in which a genetically modified individual (individual having undergone genome editing through gene transfer) of a mammal is created by subjecting a 'zygote' to 'electroporation'. For example, in Joanna B. Grabarek et al., Genesis 32 p 269-276 (2002), and Hui Peng et al., PLOS ONE vol. 7 (8) e43748 p 1-13 (2012), there is a report of an example in which DNA or dsRNA is transferred into a zygote. However, those literatures merely report 'transient' gene expression of the transferred nucleic acid.

A possible reason for the foregoing is the following problem: the related-art electroporation often uses a method involving applying an electric pulse once from an output device which employs a "decay wave system (exponential system)" (see, for example, Shimogawara, K. et al., Genetics 148 p 1821-1828 (1998)), and hence gene transfer efficiency is excessively low.

In addition, in Joanna B. Grabarek et al., and Hui Peng et al. described above, treatment with acid Tyrode's solution for removing the zona pellucida of the zygote, which poses a barrier in gene transfer, is performed for the purpose of improving the efficiency of the transfer of DNA or the like by electric pulse treatment. However, when the zygote having its zona pellucida removed or thinned is transplanted into the oviduct of a pseudopregnant female, there is a problem in that the efficiency with which the zygote undergoes normal growth into offspring remarkably decreases. That is, there is a problem in that normal growth is inhibited contrarily by performing the treatment for improving gene transfer efficiency.

In addition, as an electroporation technology for mammalian cells (cultured cells or the like), there has been disclosed a method involving applying two kinds of electric pulses to perform efficient gene transfer into mammalian cells (see Sukharev S. I. et al., Biophys. J. 63 p 1320-1327 (1992)). However, also in this method, the problem of the need to remove or thin the zona pellucida in order to realize sufficient transfer efficiency for the zygote is not alleviated.

The present invention has been made based on the findings described above.

That is, the invention according to a first aspect relates to a mammalian gene modification method, including:

immersing a zygote as defined in the following item (A) into a solution containing a nucleic acid molecule as defined in the following item (B);

applying a square-wave electric pulse as defined in the following item (C) to the solution once or two or more times so that the square-wave electric pulse has a total electric energy of from 0.2 J/100 µL to 7.5 J/100 µL;

then applying a square-wave electric pulse as defined in the following item (D) two or more times; and then applying a square-wave electric pulse as defined in the following item (E) two or more times:

(A) a pronuclear stage zygote of a mammal, except for a human, with an intact zona pellucida;

(B) RNA which functions so as to exhibit endonuclease activity against an arbitrary region of genomic DNA in a sequence-specific manner;

(C) a square-wave electric pulse having a voltage per pulse of 375 V/cm or more;

(D) a square-wave electric pulse having a voltage per pulse of 250 V/cm or less and an electric energy per pulse of from 0.01 J/100 µL to 3.6 J/100 µL; and (E) a square-wave electric pulse which is opposite in polarity to the electric pulse as defined in the item (D) and has a voltage per pulse of 250 V/cm or less and an electric energy per pulse of from 0.01 J/100 µL to 3.6 J/100 µL.

In addition, the invention according to a second aspect relates to the method according to the first aspect, in which the nucleic acid molecule as defined in the item (B) includes a nucleic acid molecule as defined in the following item (b1) and a nucleic acid molecule as defined in the following item (b2):

(b1) mRNA encoding a protein having a sequence-specific DNA-binding domain, and a domain which exhibits restriction enzyme activity when forming a dimer with a restriction enzyme activity domain as defined in the following item (b2); and (b2) mRNA encoding a protein having a sequence-specific DNA-binding domain which is a region in a vicinity of a genomic DNA region end to which the protein as defined in the item (b1) binds and which binds to a complementary strand thereof, and a domain which exhibits restriction enzyme activity when forming a dimer with the restriction enzyme activity domain as defined in the item (b1).

In addition, the invention according to a third aspect relates to the method according to the first aspect, in which the nucleic acid molecule as defined in the item (B) includes a nucleic acid molecule as defined in the following item (b3) and a nucleic acid molecule as defined in the following item (b4):

(b3) guide RNA having a complementary sequence of an arbitrary base sequence of the genomic DNA, and a sequence which specifically binds to a protein as defined in the following item (b4); and (b4) mRNA encoding a protein which exhibits endonuclease activity when specifically binding to the guide RNA as defined in the item (b3).

In addition, the invention according to a fourth aspect relates to the method according to any one of the first to third aspects, further including, after performing the electroporation, culturing the resultant zygote into a 2- to 16-cell stage embryo in a medium, and then transplanting the embryo into an oviduct or a uterus of a female of the same species or an allied species of the mammal to provide offspring.

In addition, the invention according to a fifth aspect relates to the method according to any one of the first to fourth aspects, in which the solution further contains mRNA encoding exonuclease 1 (Exo1).

In addition, the invention according to a sixth aspect relates to the method according to any one of the first to fifth aspects, in which the mammal includes a species belonging to an order Rodentia.

In addition, the invention according to a seventh aspect relates to the method according to any one of the first to sixth aspects, in which the applying of the square-wave electric pulse as defined in the item (D) is performed five or more times, and the applying of the square-wave electric pulse as defined in the item (E) is performed five or more times.

In addition, the invention according to an eighth aspect relates to the method according to any one of the first to seventh aspects, in which the gene modification causes deletion or suppression of a function by disruption of a gene.

In addition, the invention according to a ninth aspect relates to a method of creating a genetically modified individual of a mammal, including using the method of any one of the first to eighth aspects.

Advantageous Effects of Invention

The present invention enables utilization, by only an extremely simple technique, of a technology which is widely applicable to mammals without requiring the utilization of an ES cell, and which involves modifying a certain gene by targeting a certain sequence on a genome (genome editing technology based on ZFN or the like).

The present invention also enables the creation of a genetically modified individual of a mammal with high efficiency and good reproducibility without being limited to certain species of mammals.

BRIEF DESCRIPTION OF DRAWINGS

In FIG. 1, "Pp" represents a poring pulse and "Tp" represents a transfer pulse.

In FIG. 2, "Pp" represents a poring pulse and "Tp" represents a transfer pulse. The left figure is a conceptual diagram for illustrating that micropores are formed in a zona pellucida and a cell membrane by the poring pulse. The central figure is a conceptual diagram for illustrating that a transfer pulse 1 causes the mRNA to migrate into the cytoplasm of the zygote. The right figure is a conceptual diagram for illustrating that a transfer pulse 2 (pulse changed in polarity) causes the mRNA to further migrate into the cytoplasm of the zygote.

FIG. 3(A) is a photographic image of a glass chamber having mounted thereon petri dish platinum plate electrodes. FIG. 3(B) is a photographic image of the main body of an electric pulse-generating device NEPA21 (trademark).

FIG. 7 is a conceptual diagram of a TALEN designed to target a certain region of the second exon of Il2rg gene in Test Example 6.

FIG. 8 is a conceptual diagram of a CRISPR-Cas9 system designed to target a certain region of Thy gene in Test Example 7.

DESCRIPTION OF EMBODIMENTS

Figure 1:
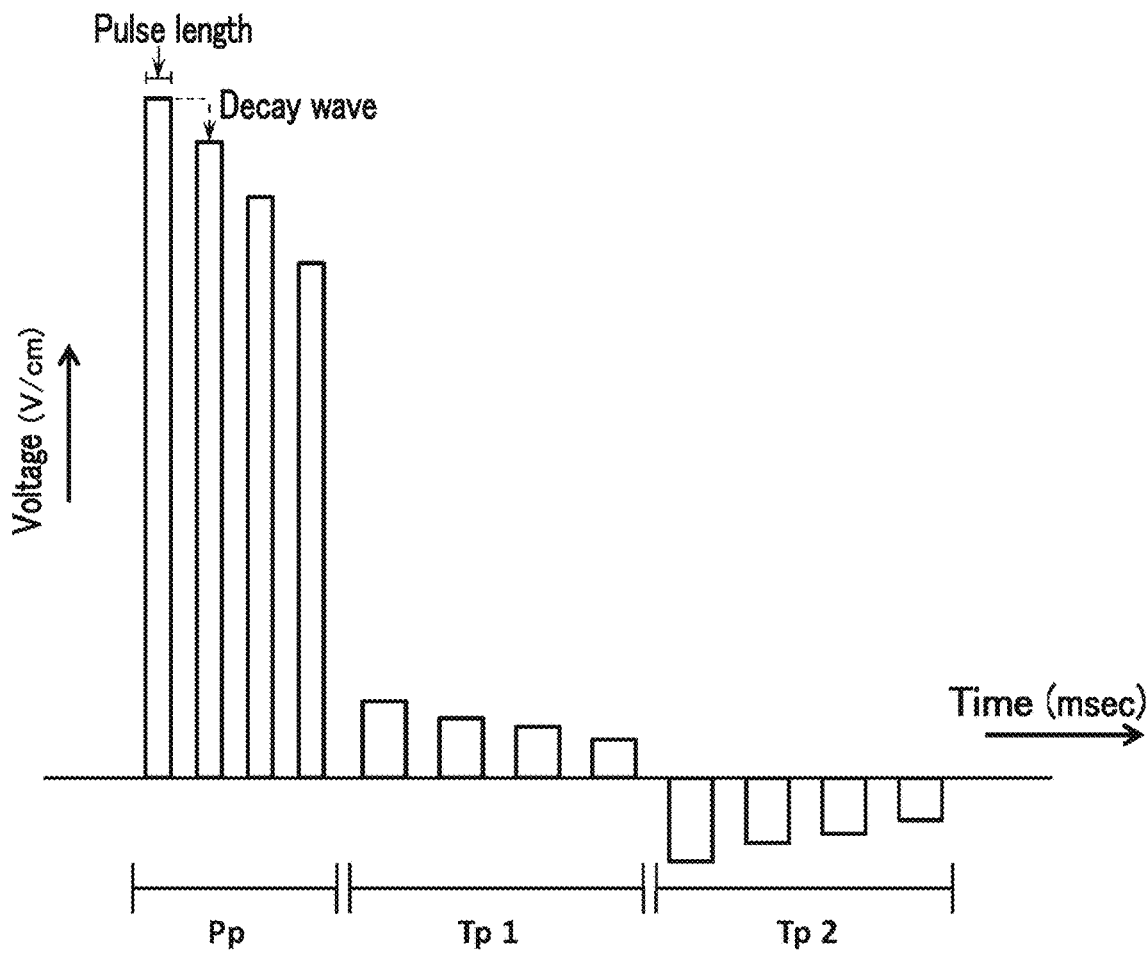
FIG. 1 is a conceptual diagram for illustrating electroporation treatment involving applying multiple square-wave pulses in three steps. The vertical axis represents a voltage (V) and the horizontal axis represents a time (msec).

Embodiments of the present invention are described in detail below.

The present invention relates to a technology for efficiently modifying an arbitrary target gene of a mammal, by immersing a pronuclear stage mammalian zygote with an intact zona pellucida into a solution containing a certain RNA molecule, and performing electroporation treatment through the application of multiple square-wave pulses in three steps with the total electric energy of a first electric pulse adjusted within a predetermined range.

[Zygote to be Subjected to Gene Transfer]

A gene modification technology of the present invention is a technology essentially using the "pronuclear stage mammalian zygote with an intact zona pellucida."

Pronuclear Stage

The zygote to be subjected to gene transfer needs to be in a "pronuclear stage (state of a pronuclear-stage embryo)." As used herein, the term 'pronuclear stage' refers to the state of a zygote in which the nucleus of a sperm has been incorporated into the cytoplasm of an egg, but the fusion of the nucleus of the egg and the nucleus of the sperm has not occurred yet. Whether or not the zygote is in a pronuclear stage may be determined through microscopy.

A method of collecting the pronuclear-stage zygote is, for example, as described below. When a female individual subjected to superovulation treatment and a male individual of the same species are allowed to mate with each other, the pronuclear-stage zygote may be collected the day after mating. Alternatively, the pronuclear-stage zygote may also be obtained artificially by subjecting an unfertilized egg collected without performing mating to intracytoplasmic sperm injection.

In the present invention, an animal in which all the cells of the individual have been genetically modified in a uniform manner can be obtained by performing gene transfer into the zygote in a pronuclear stage.

In contrast, in the case where a zygote which has passed the pronuclear stage is subjected to gene transfer, the probability of producing a chimeric individual in which cells subjected to gene transfer and cells not subjected to gene transfer are present remarkably increases, and hence such case is not preferred. In addition, in the case where the unfertilized egg is subjected to gene transfer, it becomes difficult for normal development to occur, which is not preferred.

Zona Pellucida

The zygote to be subjected to gene transfer needs to be in a "state of having a zona pellucida." As used herein, the term 'zona pellucida' refers to a matrix structure of glycoproteins which serves as an outer layer for covering and protecting an oocyte or a zygote of a mammal.

In the early development of a placental mammal, an early embryo after fertilization needs to be grown into a blastocyst while being physically protected by such structure. In this regard, the zona pellucida is recognized as a structure which plays an important role in normally growing an early embryo of a mammal.

It should be noted that the embryo after growth into the blastocyst undergoes a hatching process of breaking out of the zona pellucida and being implanted in a uterine wall, to form a placenta.

The gene modification technology of the present invention is a technology essentially involving directly performing electroporation for the zygote with an intact zona pellucida (structure posing a barrier in gene transfer). In addition, in this technology, by virtue of the protective function of the zona pellucida, the zygote after gene transfer can be transplanted into the oviduct of a female and normally grown into offspring.

As used herein, the term "zygote with an intact zona pellucida" refers to a zygote in a state of being covered with the zona pellucida (sometimes referred to a state of having a zona pellucida). With regard to the state of the zona pellucida, it is desirable that a collected zygote (or unfertilized egg) be stored as it is in a liquid medium or the like.

In addition, even when the collected zygote is subjected to cumulus cell-removing treatment (such as hyaluronidase treatment), the removal or thinning of the zona pellucida does not occur, and its protective function for the early embryo is not affected. Accordingly, in the present invention, the zygote subjected to cumulus cell-removing treatment may also be suitably used.

In contrast, in the case of a 'zygote having its zona pellucida removed or thinned' by performing acid Tyrode's treatment or the like, even when the zygote is transplanted into the oviduct of a female, it is remarkably difficult to normally grow the zygote into offspring. Accordingly, a mode involving using the 'zygote having its zona pellucida removed or thinned' is excluded from the scope of the present invention.

It should be noted that a related-art electroporation method essentially requires treatment for removing or thinning the zona pellucida (treatment for removing the barrier in gene transfer), and hence inherently involves a problem in that it becomes remarkably difficult to obtain a normally grown offspring. The present invention is recognized as an invention which provides effective means for solving the problem.

Mammal

In the early development of mammals (in particular, early development into morulae), development proceeds based on a structure and a control mechanism which are common to all mammalian species. Accordingly, the gene modification technology according to the present invention is recognized as a technology which can be employed for all mammalian species in principle. However, from an ethical point of view, the technology of the present invention should not be applied to a human (*Homo sapiens*) zygote.

As used herein, the term 'mammal' (Mammalia) refers to a monophyletic group of animals having diverged from a group of reptiles and showing a mode of behavior of rearing progeny by breastfeeding with a bodily fluid secreted from the mammary glands in the breasts (milk). Many species have body surfaces covered with body hair derived from the stratum corneum. Extant species include monotremes, marsupials, and placentals, and the vast majority of the extant species belong to the placentals.

As used herein, the term 'monotreme' (prototherian) refers to a group of mammals showing an oviparous mode of reproduction. This group is considered to be a monophyletic taxon which appeared in the Late Triassic. In this taxon, the order Monotremata (including platypuses) is the only extant order.

In addition, the term 'marsupial' (metatherian) refers to a group having an incomplete placenta and showing a mode of behavior of rearing progeny in a pouch. This group is considered to be a monophyletic taxon which appeared in the Late Cretaceous. Examples of the taxon may include the order Didelphimorphia, the order Microbiotheria, the order Dasyuromorphia, the order Peramelemorphia, the order Notoryctemorphia, and the order Diprotodontia (including kangaroos, wallabies, and koalas).

In addition, the term 'placental' (eutherian) refers to a group showing a mode of breeding of delivering progeny by childbearing through the formation of a placenta in the uterus of the mother. This group is considered to be a monophyletic group of animals which appeared in the Late Cretaceous. Examples of the taxon may include the order Macroscelidea (including elephant shrews), the order Tenrecomorpha (including tenrec and golden moles), the order Tubulidentata (including aardvarks), the order Hyracoidea (including hyraxes), the order Proboscidea (including elephants), the order Sirenia (including dugongs), the order Cingulata (including armadillos), the order Pilosa (including sloths and anteaters), the order Scandentia (including tree shrews), the order Dermoptera (including flying lemurs), the order Primates (including lemurs, monkeys, bush babies, gorillas, and chimpanzees), the order Lagomorpha (including rabbits and pikas), the order Rodentia (including mice, rats, squirrels, porcupines, and coypus), the order Erinaceomorpha (including hedgehogs), the order Soricomorpha (including moles), the order Cetacea (including whales and dolphins), the order Artiodactyla (including camels, wild boars, giraffes, deer, cattle, goats, and hippopotamuses), the order Pholidota (including pangolins), the order Carnivora (including cats, tigers, lions, dogs, wolves, weasels, raccoon dogs, foxes, bears, and seals), the order Perissodactyla (including horses, rhinoceroses, and tapirs), and the order Chiroptera (including bats).

The technology of the present invention is a technology applicable to any species among the above-mentioned mammals as long as a pronuclear-stage zygote of the species can be obtained and the species can be grown through transplantation into the uterus of a female.

For example, the technology of the present invention is a technology applicable to any species as long as a technology capable of providing offspring through pregnancy by implanting an early embryo into the oviduct or the uterus of a female through transplantation has been established for the species. In addition, even when offspring of a species cannot be obtained through embryo manipulation, the technology of the present invention is applicable to the species if a female of an allied species can be impregnated by transplantation thereinto.

This technology is expected to be a useful technology particularly for: laboratory animals, such as mice, rats, and monkeys; domestic animals, such as swine, cattle, horses, dogs, and cats; and wild animals in danger of extinction, such as elephants, tigers, and whales. In particular, in terms of elucidation of a human disease, this technology is expected to be a technology useful for animals of the order Rodentia and the order Primates.

[Nucleic Acid Molecule to be Transferred]

The technology of the present invention is a technology essentially involving transferring a predetermined nucleic acid molecule into the zygote. As used herein, the term 'predetermined nucleic acid molecule' refers to an "RNA molecule which functions so as to exhibit endonuclease activity against an arbitrary genomic DNA region in a sequence-specific manner." In addition, the term 'arbitrary genomic DNA region' refers to regions across the entirety of a genome including a regulatory region serving as a target of a transcription factor (region included in a gene in a broad sense), a spacer region, and the like as well as exons and introns in genes.

mRNA Pair Encoding ZFN Etc.

A specific example of the RNA molecule may be two kinds of mRNAs forming a pair as defined in the following items (1) and (2).

In this case, one of the two kinds of mRNAs specifically refers to (1) "mRNA encoding a protein having a sequence-specific DNA-binding domain, and a domain which exhibits restriction enzyme activity when forming a dimer with a restriction enzyme activity domain as defined in the following item (2)."

In addition, the other mRNA of the pair specifically refers to (2) "mRNA encoding a protein having a sequence-specific DNA-binding domain which is a region in the vicinity of a genomic DNA region end to which the protein as defined in the item (1) binds and which binds to a complementary strand thereof, and a domain which exhibits restriction enzyme activity when forming a dimer with the restriction enzyme activity domain as defined in the item (1)."

The proteins encoded by the mRNAs are artificial proteins which cleave an arbitrary DNA region serving as a target. The artificial proteins are each a protein having a "sequence-specific DNA-binding domain" and a "restriction enzyme activity domain," the two domains being bound to each other 'directly' or 'through the intermediation of a region serving as an adaptor.'

As used herein, the term 'sequence-specific DNA-binding domain' refers to a region of a protein which specifically binds to an arbitrary DNA sequence serving as a target.

Specific examples of the sequence-specific DNA-binding domain may include zinc finger proteins (ZFPs) and transcription activator-like effectors (TALEs).

Figure 6:
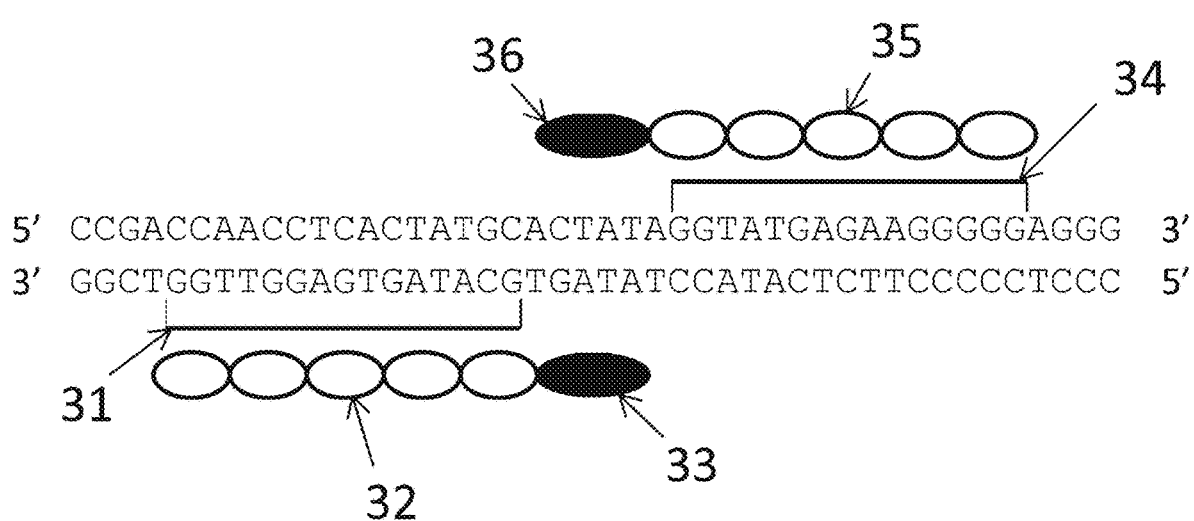
FIG. 6 is a conceptual diagram of a ZFN designed to target a certain region near the second exon of Il2rg gene in Test Example 5.

The ZFPs are each a domain which has a structure obtained by polymerizing a plurality of zinc finger units recognizing a specific three-base sequence and which recognizes and binds to a DNA sequence of a multiple of 3. The artificial protein containing any of the ZFPs is called a zinc finger nuclease (ZFN) (see FIG. 6).

In addition, the TALEs are each a domain obtained by polymerizing four kinds of units each of which recognizes and binds to any one of four kinds of bases (A, T, G, and C). The artificial protein containing any of the TALEs is called a transcription activator-like effector nuclease (TALEN) (see FIG. 7).

Those DNA-binding domains enable the design of a DNA-binding domain capable of binding to an arbitrary base sequence in a sequence-specific manner based on a combination of peptide units. In particular, the TALEs may be suitably used because of the ease of the design of an expression plasmid for mRNA preparation.

The length of a base sequence which the DNA-binding domain recognizes and binds to may be, for example, from about 8 bp to about 50 bp, preferably from 10 bp to 45 bp, more preferably from 13 bp to 40 bp, still more preferably from 14 bp to 30 bp, particularly preferably from 15 bp to 25 bp, even more preferably from 15 bp to 21 bp. The case where the length of the recognition sequence is excessively short is not desirable because sequence specificity is decreased to increase mismatch binding. The case where the length of the recognition sequence is excessively long is not preferred because the molecular weight of the mRNA encoding the peptide is increased to decrease transfer efficiency.

It should be noted that, in this technology, the DNA-binding domains of the items (1) and (2) need to be designed so as to bind to sites interposing therebetween the recognition sequence for a restriction enzyme activity unit and to bind to such sites that the restriction enzyme activity domains of the items (1) and (2) can form a dimer.

In addition, in this technology, the "sequence-specific DNA-binding domain as defined in the item (2)" needs to be a region in the vicinity of a DNA region end to which the protein as defined in the item (1) binds and to bind to a complementary strand thereof.

As used herein, the term 'vicinity' means such a site that, when the proteins of the items (1) and (2) bind to DNA, their domains having restriction enzyme activity are separated by a certain distance so as to be able to form a dimer. Such site is desirably, for example, such a site that ends of the DNA regions to which the proteins of the items (1) and (2) bind are separated from each other by a certain distance of from about 4 bp to about 50 bp.

The "restriction enzyme activity domain" in this technology refers to a region which exhibits restriction enzyme activity only when the restriction enzyme activity domains as defined in the items (1) and (2) form a dimer with each other. That is, the restriction enzyme activity domains each do not exhibit activity alone, but exhibit sequence-specific endonuclease activity only when forming a dimer.

The domains preferably exhibit type II restriction enzyme activity. Specifically, FokI, a FokI mutant, or the like is suitably used. It should be noted that the FokI mutant refers to a protein having an amino acid sequence having a substitution, a deletion, an insertion, and/or an addition (addition to an end) in the amino acid sequence of FokI. Specifically, the FokI mutant refers to a protein containing an amino acid sequence having a homology of 90% or more, preferably 95% or more, more preferably 98% or more, still more preferably 99% or more to the amino acid sequence of FokI, the protein having a function equivalent to or higher than that of FokI.

The length of the mRNA is 0.3 kb or more, preferably 0.5 kb or more, more preferably 0.8 kb or more, still more preferably 1 kb or more in ordinary cases. In addition, the case where the mRNA is excessively long and has a high molecular weight is not suitable because the efficiency of transfer into the zygote is decreased. It is desirable that the length be, for example, 5 kb or less, preferably 4 kb or less, more preferably 3 kb or less.

Each of the mRNAs transferred into the zygote is translated by the protein synthesis system of the cell to synthesize an artificial protein. The artificial protein as defined in the item (1) and the artificial protein as defined in the item (2) produced in the zygote bind to genomic DNA at sites interposing therebetween a cleavage site located in the target region to cleave the DNA.

It should be noted that, in the technology of the present invention, when DNA (specifically plasmid DNA) is used as the nucleic acid molecule, a desired genetically modified individual cannot be obtained. For example, as shown in an example of the transfer of plasmid DNA in Test Examples to be described later, a normally grown genetically modified individual cannot be created. A possible reason therefor is that the transcription system of the zygote hardly functions sufficiently and the artificial protein which is a translation product is hardly produced sufficiently.

RNA for CRISPR-Cas9 System

Another example of the RNA to be transferred in the technology of the present invention may be guide RNA as defined in the following item (3) and mRNAs defined in the following item (4) which constitute a CRISPR-Cas9 system.

It should be noted that the term 'CRISPR' as used herein is an acronym for clustered regularly interspaced short palindromic repeats, and refers to a DNA region functioning as an acquired immune mechanism against a phage or a plasmid in a prokaryote.

The guide RNA constituting the CRISPR-Cas9 system specifically refers to (3) "guide RNA having a complementary sequence of an arbitrary base sequence of genomic DNA, and a sequence which specifically binds to a protein as defined in the following item (4)."

The guide RNA is an RNA molecule having a 'complementary sequence' to an arbitrary base sequence designed in an arbitrary genomic DNA region. The guide RNA suitably has its 5' side (preferably 5' end) constituted of the complementary sequence. Through the hybridization of the complementary sequence to a target genome sequence, the guide RNA can bind to the genomic DNA in a sequence-specific manner.

In this connection, the 'arbitrary base sequence' to which the complementary sequence hybridizes is suitably a base sequence immediately upstream of a PAM sequence (recognition sequence for Cas9). It is particularly suitable that the 3' end of the 'arbitrary base sequence' and the 5' end of the PAM sequence be adjacent to each other. In addition, in order to avoid mismatch binding, it is important to design the sequence in consideration of the absence of an analogous sequence in the genomic DNA.

In addition, it is desirable that the length of the arbitrary base sequence be from 15 bp to 40 bp, preferably from 15 bp to 30 bp, more preferably from 15 bp to 25 bp, still more preferably from 18 bp to 22 bp, particularly preferably about 20 bp. The case where the sequence is excessively short is not suitable because mismatch binding is liable to occur.

In addition, the guide RNA contains, on the 3' side of the complementary sequence, a sequence which specifically binds to the protein as defined in the item (3). The specific binding is presumably realized by virtue of a certain RNA sequence and a certain RNA three-dimensional structure.

An example of the certain RNA sequence on the 3' side of the guide RNA may be an RNA sequence (see SEQ ID NO: 8) constituting the 3' side of the above-mentioned complementary sequence in crRNA:tracrRNA of CRISPR, or an analogous sequence thereof.

Herein, the analogous sequence of crRNA:tracrRNA refers to an RNA sequence having a base sequence having a substitution, a deletion, an insertion, and/or an addition (addition to an end) in the base sequence of SEQ ID NO: 8. Specifically, the analogous sequence refers to an RNA sequence containing a base sequence having an identity of 80% or more, preferably 85% or more, more preferably 90% or more, still more preferably 95% or more, particularly preferably 98% or more, even more preferably 99% or more to the base sequence of SEQ ID NO: 8, the RNA sequence having a function equivalent to or higher than that of crRNA:tracrRNA of SEQ ID NO: 8.

The mRNA constituting the CRISPR-Cas9 system specifically refers to (4) "mRNA encoding a protein which exhibits endonuclease activity when specifically binding to the guide RNA as defined in the item (3)."

The protein encoded by the mRNA is a protein which specifically binds to the guide RNA to cleave an arbitrary target DNA sequence. A specific example of the protein may be a Cas9 nuclease or an analogous protein thereof.

The Cas9 nuclease is a protein which recognizes a certain base sequence called a proto-spacer adjacent motif (PAM) and exhibits activity of cleaving DNA in a target sequence upstream thereof (endonuclease activity) (see FIG. 8). It should be noted that the PAM sequence may vary depending on the kind of bacteria from which the Cas9 nuclease is derived. For example, in the case of a Cas9 nuclease derived from *Streptococcus pyogenes* (SpCas9), a PAM sequence "NGG" is recognized. In addition, in the case of a Cas9 nuclease derived from *S. thermophiles* (StCas9), a PAM sequence "NNAGAAW" is recognized. In addition, there is also a report of a kind of Cas9 which recognizes a PAM sequence "NNNNGATT".

In addition, the analogous protein of the Cas9 nuclease refers to a protein having an amino acid sequence having a substitution, a deletion, an insertion, and/or an addition (addition to an end) in the amino acid sequence of SpCas9 (Cas9 nuclease derived from *S. pygenes*) or StCas9 (Cas9 nuclease derived from *S. thermophiles*). Specifically, the analogous protein of the Cas9 nuclease refers to a protein containing an amino acid sequence having a homology of 80% or more, preferably 85% or more, more preferably 90% or more, still more preferably 95% or more, particularly preferably 98% or more, even more preferably 99% or more to the amino acid sequence of SpCas9 or StCas9, the protein having a function equivalent to or higher than that of SpCas9 or StCas9. The analogous protein also encompasses an artificially produced Cas9 mutant protein.

The mRNA as defined in the item (4) transferred into the zygote is translated by the protein synthesis system of the cell to synthesize the protein encoded by the mRNA. The protein as defined in the item (4) binds to the guide RNA as defined in the item (3) binding to a genomic DNA sequence serving as a target and exhibits activity of cleaving DNA in a target sequence upstream of the PAM sequence (see FIG. 8).

It should be noted that, in the technology of the present invention, when DNA (specifically plasmid DNA) is used as the nucleic acid molecule, a desired genetically modified individual cannot be obtained. A possible reason therefor is that the transcription system of the zygote hardly functions sufficiently and the protein which is a translation product is hardly produced sufficiently.

Exonuclease 1 (Exo1)

In this technology, it is desirable that "mRNA encoding exonuclease 1 (Exo1)" be cotransferred separately from the above-mentioned RNA molecule. Through the cotransfer of the Exo1 mRNA, recombination efficiency of the target gene can be significantly improved.

[Electroporation Treatment]

The technology of the present invention is a technology essentially involving: immersing the zygote into a solution containing a nucleic acid molecule; and subjecting the zygote to treatment involving applying multiple square-wave pulses in three steps which satisfy predetermined electric pulse conditions (electroporation treatment).

Device

In order to perform the electroporation treatment, any device may be used as long as the device can output multiple square-wave pulses in three steps that satisfy predetermined electric pulse conditions to be described later.

For example, an electric pulse-outputting device "NEPA21 (trademark)" from Nepa Gene Co., Ltd. may be suitably used. This device has a function of measuring an electrical impedance value and a current value for each treatment, and hence electric conditions can be set in detail. The device also has a function of switching electrical polarity for each electric pulse when applying multiple electric pulses.

It should be noted that, although the electroporation may be performed by devising a way to use a conventional square pulse system electric pulse-outputting device, this is not suitable because electric energy at the time of the electroporation cannot be determined from the viewpoint of a limitation on the function of the device.

Electroporation Buffer

The electroporation treatment is performed by preparing a solution having dissolved therein the nucleic acid molecule and applying electric pulses to energize the solution.

Herein, a buffer solution, such as phosphate buffered saline (PBS), or a general medium for zygotes may be used as the solution (electroporation buffer). That is, there is no need to purchase or prepare any special electroporation buffer.

It is suitable that the concentration of the nucleic acid molecule to be incorporated in the solution be 0.5 ng/µL or more, preferably 1 ng/µL or more, more preferably 2 ng/µL or more, still more preferably 5 ng/µL or more, particularly preferably 10 ng/µL or more, even more preferably 20 ng/µL or more, still even more preferably 30 ng/µL or more, yet still even more preferably 40 ng/µL or more for each RNA. The case where the nucleic acid concentration is excessively low is not preferred because gene transfer efficiency is lowered.

It is suitable that the upper limit of the nucleic acid concentration be 2,000 ng/µL or less, preferably 1,500 ng/µL or less, more preferably 1,000 ng/µL or less, still more preferably 750 ng/µL or less, particularly preferably 500 ng/µL or less, even more preferably 400 ng/µL or less for each mRNA. The case where the nucleic acid concentration is excessively high is not preferred because the survival rate of the zygotes is lowered, resulting in a decrease in the number of offspring to be obtained.

It should be noted that the concentration ratio of RNAs when two kinds of RNAs are added is suitably adjusted to, in terms of molar ratio, from 1:0.1 to 1:10, preferably from 1:0.2 to 1:8, more preferably from 1:0.4 to 1:6, still more preferably from 1:0.6 to 1:1.4, particularly preferably from 1:0.8 to 1:1.2, even more preferably about 1:1.

It should be noted that the solution is desirably free of an antibiotic. This is because, when an antibiotic is present in the solution, the antibiotic is incorporated into the cell through the electroporation treatment to decrease the survival rate of the cell.

Further, the solution is desirably also free of serum. This is because, when serum is present in the solution, the serum inhibits the incorporation of the nucleic acid molecule into the cell at the time of the electroporation treatment to decrease transfer efficiency. It should be noted that the incorporation of the serum is permitted as long as its concentration is low (e.g., 1% or less, preferably 0.5% or less).

Electrodes

The electroporation treatment is performed using electrodes connected to an electric pulse-outputting device. Any kind of electrodes may be used in principle, and specifically, petri dish electrodes, chamber electrodes, needle electrodes, tweezer-style electrodes, cuvette electrodes, and the like may be used. Of those electrodes, specifically, petri dish electrodes, chamber electrodes, and the like are suitably used. As the electrodes, ones in accordance with a general standard may be used, and for example, ones having an interelectrode distance (gap) of from 2 mm to 50 mm, preferably from 5 mm to 25 mm may be used.

The electroporation treatment is performed by: bringing the electrodes into a state of being immersed into the 'solution having dissolved therein the nucleic acid molecule'; immersing the zygote into the solution so as to establish a resting state; and applying electric pulses. Specifically, it is desirable that the electroporation treatment be performed by immersing the zygote between the positive pole and the negative pole of the electrodes to establish a resting state and applying electric pulses. It is desirable that a plurality of the zygotes be placed at rest in parallel with a line connecting the electrodes to avoid overlaps of zygotes.

Electric Pulse Treatment

Electric pulses output from the electric pulse-outputting device are conducted to the zygote placed at rest between the electrodes.

It should be noted that the electroporation treatment is suitably performed at room temperature (e.g., from about 10° C. to about 35° C.). In addition, it is recommended to avoid cooling with ice in order to prevent a water droplet from adhering to a metal part of the electrode.

[Electric Pulse Conditions]

Figure 2:
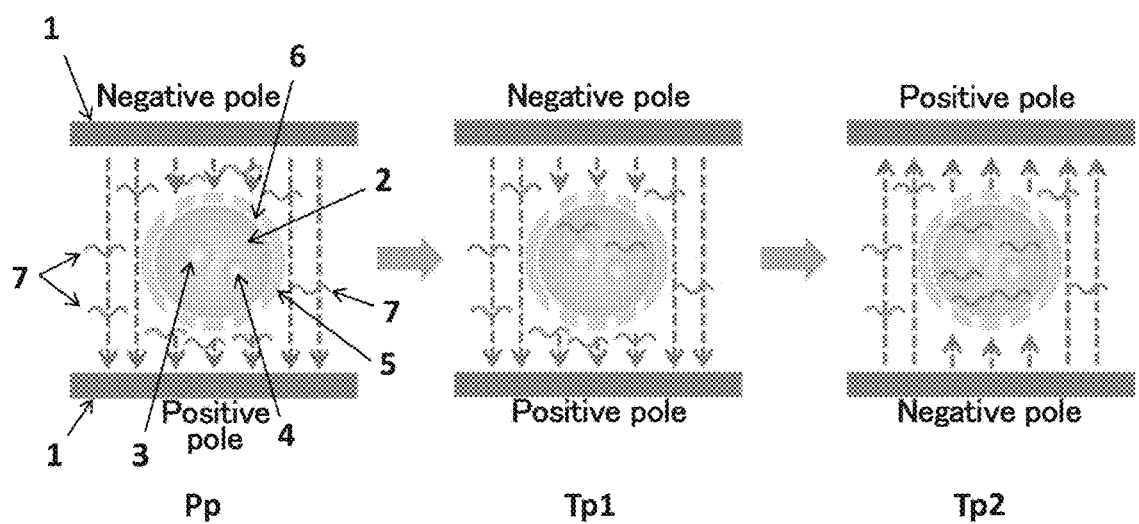
FIG. 2 are conceptual diagrams for illustrating a mechanism by which mRNA is transferred into a zygote through electroporation treatment involving applying multiple square-wave pulses in three steps.

The method of the present invention includes performing electroporation using multiple square-wave pulses by the following three steps: applying a square-wave electric pulse (first electric pulse) with a high voltage for a short period of time under predetermined conditions to the solution containing the nucleic acid molecule in which the zygotes are placed at rest; then applying a square-wave electric pulse (second electric pulse) with a low voltage for a long period of time to the solution two or more times; and then applying a square-wave electric pulse (third electric pulse) that is opposite in polarity to the second electric pulse, with a low voltage for a long period of time, to the solution two or more times (see, for example, FIG. 1 and FIG. 2).

It is required that both the 'voltage' and 'electric energy' of each of the first to third electric pulses in the present invention fall within certain ranges to be described later.

The voltage as used herein is a value representing a voltage V to be applied per unit cm of the width between electrodes. For example, in order to apply a voltage of 300 V/cm using a 5 mm gap electrode, the voltage to be applied is 150 V. In addition, the electric energy (W) as used herein is a value representing electric energy (energy amount) to be applied per 100 μL of the solution. For example, when a voltage (V) of 150 V is applied to 100 μL of a solution having an impedance value of 50Ω for a time (T) of 5 msec in terms of pulse length, a current (I) of 3 A is generated. In this case, the electric energy (W=VIT) to be applied per 100 μL of the solution is 2.25 J.

In addition, it is required to apply 'square-wave' electric pulses as the electric pulses of the present invention. With 'decay wave' electric pulses, a high gene transfer efficiency to be attained in the present invention cannot be realized.

First Electric Pulse: Poring Pulse (Pp)

The electroporation treatment of the present invention is a technology essentially involving applying the square-wave electric pulse (first electric pulse: poring pulse) with a high voltage for a short period of time under predetermined conditions. Through the application of the first electric pulse, small pores can be formed in the zona pellucida with a small degree of damage.

It should be noted that, in a general electroporation method for animal cells (conventional method), although there is a finding that increasing the voltage of the first electric pulse allows a nucleic acid molecule (e.g., DNA) to be transferred into cells, gene transfer at a practical level cannot be attained for zygotes by merely increasing the voltage. This is probably because when the damage to the zona pellucida is severe, the survival rate of the zygotes subjected to the electroporation treatment remarkably decreases, and normal growth of early embryos is remarkably inhibited.

In the first electric pulse, it is necessary to apply a voltage of at least 375 V/cm or more (187.5 V or more in the case of a 5 mm gap electrode). It is desirable to apply a voltage of preferably 400 V/cm or more, more preferably 450 V/cm or more, still more preferably 500 V/cm or more. The case where the voltage is excessively low is not preferred because small pores cannot be formed in the zona pellucida.

It should be noted that the first electric pulse may be applied without any particular limitation on the upper limit of its voltage value as long as a condition for the total electric energy to be described later is satisfied. This is because the degree of damage to the zona pellucida mainly depends on the value of the 'total electric energy (energy amount).' It should be noted that the upper limit value, if given anyway, may be, for example, 4,500 V/cm or less, preferably 3,750 V/cm or less, more preferably 2,500 V/cm or less, still more preferably 1,500 V/cm or less.

The condition for the total electric energy corresponds to a condition for suppressing damage to the zona pellucida and the cell membrane while forming, in the zona pellucida, small pores suitable for the incorporation of nucleic acids.

It is essential that the 'total electric energy' of the first electric pulse fall within a predetermined range. In this context, the total electric energy is a value showing the total value of the electric energy of electric pulses each having the above-mentioned voltage value or higher. For example, when an electric pulse of 750 V/cm or more is applied two times, the total value of the electric energy of the two times of electric pulses is defined as the value of the total electric energy.

It is essential that the total electric energy be 0.2 J/100 µL or more. When the total electric energy is excessively low, sufficient gene transfer efficiency cannot be attained. The lower limit of the total electric energy may be, for example, preferably 0.286 J/100 µL or more, more preferably 0.3 J/100 µL or more, still more preferably 0.4 J/100 µL or more, particularly preferably 0.5 J/100 µL or more, even more preferably 0.535 J/100 µL or more, still even more preferably 0.558 J/100 µL or more.

In addition, it is essential that the upper limit of the total electric energy be 7.5 J/100 µL or less. The case where the total electric energy is excessively high is not preferred because damage to the zona pellucida or the cell membranes increases, resulting in a decrease in survival rate. The upper limit of the total electric energy may be, for example, preferably 7.317 J/100 µL or less, more preferably 7.3 J/100 µL or less, still more preferably 7 J/100 µL or less, particularly preferably 6.5 J/100 µL or less, even more preferably 6 J/100 µL or less, still even more preferably 5.5 J/100 µL or less, yet still even more preferably 5 J/100 µL or less, more particularly preferably 4.5 J/100 µL or less, furthermore preferably 4.3 J/100 µL or less, still further more preferably 4.255 J/100 µL or less.

The condition for the total electric energy corresponds to a condition for suppressing damage to the zona pellucida and the cell membranes while forming, in the zona pellucida, small pores suitable for the incorporation of a nucleic acid.

It should be noted that the first electric pulse may be applied without any particular limitation on the number of times of its application as long as the total electric energy falls within the above-mentioned range. For example, the electric pulse may be applied at one time within the above-mentioned range of the electric energy, or the electric pulse may be applied two or more times by dividing the electric energy. Specifically, the number of the times may be, for example, 2 to 20. With the electric pulse is applied a plurality of times with the divided electric energy, an effect of slightly reducing the degree of damage to the zona pellucida is expected. The number of times may be, for example, preferably 3 or more, more preferably 4 or more. The upper limit of the number of times is not particularly limited, but may be, for example, preferably 15 or less, more preferably 10 or less, still more preferably 5 or less.

It should be noted that an interval between pulses in the case of the plurality of times of the application of the pulse may be, for example, 200 msec or less, preferably 100 msec or less, more preferably 75 msec or less, still more preferably 50 msec or less.

In addition, in the present invention, the pulse length and decay rate of the first electric pulse are factors for determining the electric energy, but do not show direct correlations with the gene transfer efficiency and the survival rate.

Second Electric Pulse: Transfer Pulse 1 (Tp1)

The electroporation treatment of the present invention is a technology essentially involving applying, after the application of the first electric pulse (after the last output of the first electric pulse), a square-wave electric pulse (second electric pulse: transfer pulse 1) with a low voltage for a long period of time under predetermined conditions. This is because, by virtue of the second electric pulse, the nucleic acid molecule is efficiently incorporated into the cells through the small pores (pores in the zona pellucida formed by the first electric pulse). It should be noted that the second electric pulse is a low-electric energy pulse having a low energy amount, and hence is free of a risk of causing damage to the zygotes.

It should be noted that the electrical polarity of the second electric pulse may be the same electrical polarity (the direction of the electrodes is the same) as or may be the opposite polarity (the direction of the electrodes is opposite) to that of the first electric pulse, but it is desirable that the electric pulses preferably have the same polarity.

In the second electric pulse, it is necessary to apply a voltage under a condition of 250 V/cm or less (125 V or less in the case of a 5 mm gap electrode). It is desirable to apply a voltage of preferably 240 V/cm or less, more preferably 225 V/cm or less, still more preferably 200 V/cm or less, particularly preferably 175 V/cm or less, even more preferably 150 V/cm or less, still even more preferably 125 V/cm or less. The case where the voltage is excessively high is not suitable because damage to the zona pellucida increases, resulting in a decrease in survival rate.

It should be noted that the second electric pulse may be applied without any particular limitation on the lower limit of the voltage value thereof as long as a condition for its electric energy per pulse to be described later is satisfied, but the lower limit value, if given anyway, may be, for example, 15 V/cm or more, preferably 20 V/cm or more, more preferably 25 V/cm or more, still more preferably 30 V/cm or more, particularly preferably 35 V/cm or more.

It is essential that the 'electric energy per pulse' of the second electric pulse fall within a predetermined range. It is essential that the electric energy be 0.01 J/100 µL or more. When the electric energy is excessively low, sufficient gene transfer efficiency cannot be attained. The lower limit of the electric energy may be, for example, preferably 0.012 J/100 µL or more, more preferably 0.02 J/100 µL or more, still more preferably 0.03 J/100 µL or more, particularly preferably 0.034 J/100 µL or more, even more preferably 0.04 J/100 µL or more, still even more preferably 0.05 J/100 µL or more, yet still even more preferably 0.06 J/100 µL or more, more particularly preferably 0.07 J/100 µL or more, further more preferably 0.08 J/100 µL or more, still further more preferably 0.1 J/100 µL or more.

In addition, it is essential that the upper limit of the total electric energy be 3.6 J/100 µL or less. The case where the electric energy is excessively high is not preferred because damage to the zona pellucida increases, resulting in a decrease in survival rate. The upper limit of the electric energy may be, for example, preferably 3.571 J/100 µL or less, more preferably 3 J/100 µL or less, still more preferably 2.5 J/100 µL or less, particularly preferably 2.286 J/100 µL or less, even more preferably 2 J/100 µL or less, still even more preferably 1.75 J/100 µL or less, yet still even more preferably 1.5 J/100 µL or less, more particularly preferably 1.25 J/100 µL or less, further more preferably 1 J/100 µL or less, still further more preferably 0.8 J/100 µL or less, yet still further more preferably 0.7 J/100 µL or less, still more particularly preferably 0.679 J/100 µL or less, even yet still further more preferably 0.6 J/100 µL or less, yet still more particularly preferably 0.556 J/100 µL or less.

In the technology of the present invention, it is required that the second electric pulse be applied two or more times. It is suitable that the number of the times be preferably 3 or more, more preferably 4 or more, still more preferably 5 or more, particularly preferably 6 or more, even more preferably 7 or more, still even more preferably 8 or more, yet still even more preferably 9 or more, more particularly preferably 10 or more. Increasing the number of the times of the second electric pulse allows the incorporation of the nucleic acid molecule through the small pores to be performed many times, and hence transfer efficiency can be improved.

The upper limit of the number of the times, which is not particularly limited, may be, for example, 30 or less, preferably 25 or less, more preferably 20 or less. Even when the number of the times is increased any further, the efficiency cannot be expected to be improved greatly.

It should be noted that an interval between pulses in the case of the plurality of times of the application of the pulse may be, for example, 200 msec or less, preferably 100 msec or less, more preferably 75 msec or less, still more preferably 50 msec or less.

In addition, in the present invention, the pulse length and decay rate of the second electric pulse are factors for determining the electric energy, but do not show direct correlations with the gene transfer efficiency and the survival rate.

Third Electric Pulse: Transfer Pulse 2 (Tp2)

The electroporation treatment of the present invention is a technology essentially involving applying, after the application of the second electric pulse (after the last output of the second electric pulse), a square-wave electric pulse (third electric pulse: transfer pulse 2) that is opposite in electrical polarity (the direction of the electrodes is opposite) to the second electric pulse, with a low voltage for a long period of time under predetermined conditions.

By virtue of the third electric pulse, even after the completion of the incorporation of the nucleic acid molecule into the cells with the second electric pulse, the nucleic acid molecule can be further incorporated. That is, transfer efficiency can be significantly improved. It should be noted that the third electric pulse, as with the second electric pulse, is also a low-electric energy pulse having a low energy amount, and hence is an electric pulse free of a risk of causing damage to the zygotes.

The third electric pulse is, except for being opposite in electrical polarity, an electric pulse applied under the same conditions as the second electric pulse. That is, as various electric conditions of the third electric pulse, the same conditions as the conditions described above for the second electric pulse may be adopted.

Pulse Interval Between Electric Pulses Having Different Properties

The Pp, the Tp1, and the Tp2 are electric pulses having electric pulse properties different from each other, but a general pulse interval may be adopted as an interval between the pulses. The interval is not particularly limited, but may be, for example, 200 msec or less, preferably 100 msec or less, more preferably 75 msec or less, still more preferably 50 msec or less.

[Transplantation of Zygote]

The zygote subjected to the electroporation treatment is artificially cultured into an early embryo, and then transplanted into the uterus (oviduct or uterus) of a female, thereby being able to be grown in the uterus of the female. In this case, it is preferred that the culture of the early embryo be performed into a 2- to 16-cell stage embryo, preferably a 2- to 8-cell stage embryo, more preferably a 2- to 4-cell stage embryo, still more preferably a 2-cell stage embryo. The case where development by the culture excessively proceeds is not preferred because the number of individuals to be grown into normal offspring is reduced.

As a female serving as a parent which is a recipient of transplantation, an individual from which the zygote has been collected (donor) itself may be used, but another female individual of the same species as the donor is suitably used. It should be noted that, in the case of a rodent, pseudopregnancy treatment (mating treatment with a vasectomised male) may need to be performed.

In addition, even in the case of a species for which there is no established pregnancy technology based on embryo transplantation, if a female of an allied species can be impregnated, offspring can be thus obtained.

It should be noted that the case where the zona pellucida of the zygote is removed before transplantation is not preferred because the birth rate of the offspring is remarkably decreased.

After the pregnancy, normally grown offspring can be obtained by allowing the female to undergo spontaneous delivery (laying of eggs in the case of a monotreme). The offspring thus obtained include, at a high probability, an individual in which the desired gene on the genomic DNA described above has been modified.

That is, a genetically modified individual of a mammal can be efficiently obtained.

[Genetically Modified Individual]

The offspring obtained by this technology is an individual in which only an arbitrary region in genomic DNA has been modified. That is, an individual in which an arbitrary target gene (or an arbitrary spacer region) has been modified can be obtained.

Whether or not the offspring is a genetically modified individual (or an individual in which a spacer region has been modified) can be simply determined by: extracting genomic DNA from blood; performing PCR involving using primers interposing therebetween the target sequence; and (i) examining the length of an amplified fragment by electrophoresis or (ii) reading the sequence by sequencing.

In the technology of the present invention, through the transfer of the RNA molecule into the zygote, a sequence in a target region of genomic DNA is specifically cleaved by the function of the RNA molecule, and then the cleaved site is repaired by an endogenous enzyme. At this time, a deletion mutation or an insertion mutation occurs, and the offspring thus obtained is an individual in which the target gene has been knocked out.

In the present invention, based on such principle, the function of a genomic DNA region serving as a target can be disrupted to provide an individual having the function of the gene deleted or an individual having the function of the gene suppressed.

In addition, in the present invention, through the utilization of this technology and homologous recombination, a target gene can be functionally modified by artificially inducing homologous recombination. That is, a knockin individual can be obtained.

In this case, in the electroporation treatment, a DNA fragment having a "DNA sequence which is a homologous sequence of a target region containing a cleavage site and involves a desired mutation, such as a base substitution" needs to be cotransferred separately from the above-mentioned RNA.

Offspring obtained by such treatment include an individual having the target gene functionally modified by artificial homologous recombination.

EXAMPLES

The present invention is hereinafter described by way of Examples. However, the scope of the present invention is not limited to these Examples.

In addition, in the following tables, the "+" sign indicating the polarity of a transfer pulse was used as a sign showing an electric pulse having the same polarity as a poring pulse.

In addition, the "−" sign was used as a sign showing that an electric pulse opposite in polarity to the poring pulse was applied.

In addition, in the following tables, the voltage value (V) of an electric pulse was expressed in terms of value per 1 cm (V/cm). In addition, an energy value (J) was expressed in terms of value per 100 μL (J/100 μL).

[Test Example 1 (Investigation Example)] "Test for Compound Transfer into Pronuclear-Stage Zygote with Intact Zona Pellucida"

An investigation was made of whether or not an exogenous compound was able to be transferred into a pronuclear-stage zygote with an intact zona pellucida by performing electroporation based on a square-wave three-step method.

(1) "Collection of Zygote"

Mature female rats (8- to 16-week-old) of the F344/Stm strain (NBRP-Rat, Kyoto, Japan) were injected with pregnant mare serum gonadotropin (PMSG, ASKA Pharmaceutical Co., Ltd.) at 150 IU/kg of body weight, and 48 hours after that, were injected with human chorionic gonadotropin (hCG, ASKA Pharmaceutical Co., Ltd.) at 75 IU/body weight to induce superovulation.

The females were allowed to cohabit and mate with males (11-week-old) of the same strain. The next day, pronuclear-stage zygotes were collected, and hyaluronidase treatment was performed to remove cumulus cells. The collected zygotes were stored in a modified Krebs-Ringer solution.

It should be noted that breeding of the rats was managed under the temperature condition of 24±2° C., the humidity condition of 50±10%, and the light condition of a light period of from 7 AM to 7 PM.

(2) "Electric Pulse Treatment"

Figure 3:
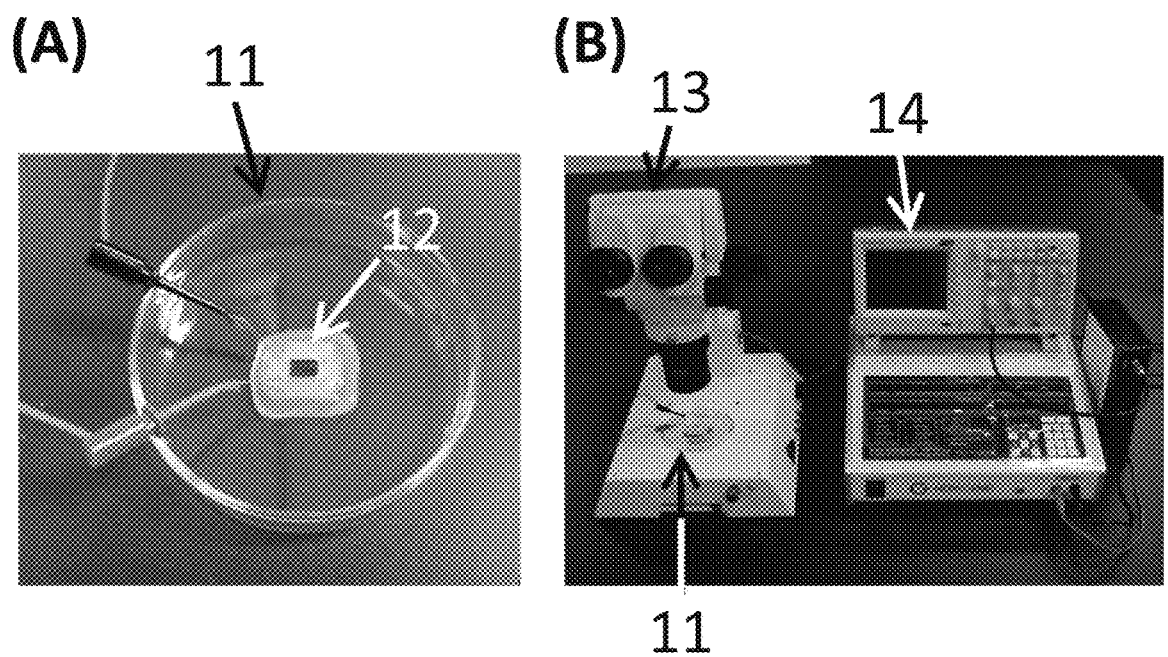
FIG. 3 are photographic images taken of an electric pulse-generating device used in Examples.

Between petri dish platinum plate electrodes (CUY520P5, 5 mm gap, L10×W5×H5 mmm, manufactured by Nepa Gene Co., Ltd.) on a glass chamber, 100 μL of phosphate buffered saline (PBS) containing 2 mg/mL tetramethylrhodamine-labeled dextrin was injected, and the collected pronuclear-stage zygotes were placed at rest in a line between the phosphate buffer saline-charged metal plate electrodes (see FIG. 3(A)). In this case, the pronuclear-stage zygotes were used while keeping the state at the time of being collected without being subjected to zona pellucida-removing and thinning treatment.

It should be noted that the tetramethylrhodamine-labeled dextrin used was a fluorescent substance having a molecular weight of 3 kDa and manufactured by Life Technologies Co.

To the metal plate, an electric pulse-generating device (NEPA21 (trademark), manufactured by Nepa Gene Co., Ltd.) capable of generating square-wave electric pulses was connected (see FIG. 3(B)), and electric pulse treatment was performed based on the electroporation method involving using multiple pulses by the three steps of sequentially applying three kinds of square-wave electric pulses, i.e., the poring pulse (Pp), the transfer pulse 1 (Tp1), and the transfer pulse (Tp2) (see FIG. 1). The respective conditions for the electric pulses were set to the conditions shown in Table 1. It should be noted that the series of operations was performed under a room temperature condition in order to prevent a water droplet from adhering.

On the other hand, as a control, between petri dish platinum plate electrodes, 100 μL of general phosphate buffered saline (PBS) containing no tetramethylrhodamine-labeled dextrin was injected, and electric pulse treatment was similarly performed.

(3) "Observation with Fluorescence Microscope"

Figure 4:
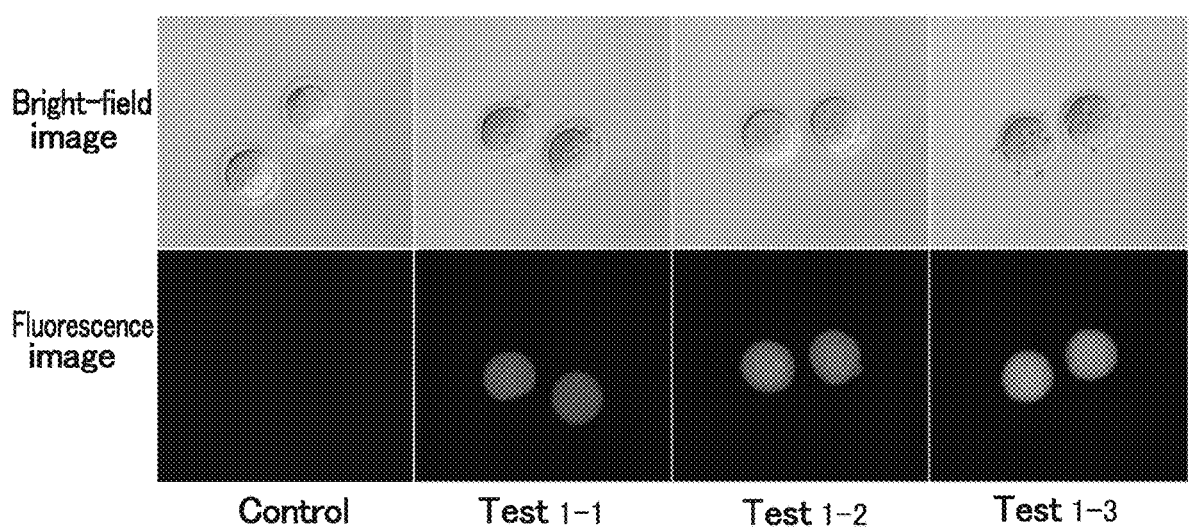
FIG. 4 are photographic images taken of zygotes into which tetramethylrhodamine-labeled dextrin has been transferred in Test Example 1. Photographic images in the upper row are photographic images taken with a microscope in a bright field. Photographic images in the lower row are photographic images taken with a fluorescence microscope.

Photographic images were taken of the zygotes after the electric treatment with a fluorescence microscope (Olympus Co., Tokyo, Japan) by applying excitation light at 541 nm with a 520 nm to 550 nm filter and detecting fluorescence at 572 nm with a 580 nm transmission filter. The results are shown in FIG. 4.

(4) "Results"

From the results, it was shown that tetramethylrhodamine fluorescence was detected from the whole cytoplasm of a zygote by applying an electric pulse with a high voltage for a short period of time to the zygote with an intact zona pellucida under the electric conditions shown in Table 1 and then applying electric pulses with a low voltage for a long period of time while changing the polarity between Tp1 and Tp2 (Tests 1-1 to 1-3).

From the results, it was shown that the exogenous compound was able to be efficiently transferred into a pronuclear-stage zygote with an intact zona pellucida by performing electroporation based on the three-step multiple square-wave pulse method.

TABLE 1

|  |  | Test 1-1 | Test 1-2 | Test 1-3 |
|---|---|---|---|---|
|  | Interelectrode gap (mm) | 5 | 5 | 5 |
|  | Liquid volume (μL) | 100 | 100 | 100 |
| Pp | Voltage (V/cm) | 450 | 450 | 450 |
|  | Pulse length (msec) | 0.5 | 1.5 | 2.5 |
|  | Pulse interval (msec) | 50 | 50 | 50 |
|  | Number of pulses (times) | 4 | 4 | 4 |
|  | Decay rate (%) | 10 | 10 | 10 |
|  | Pulse interval (msec) | 50 | 50 | 50 |
| Tp1 | Voltage (V/cm) | 40 | 40 | 40 |
| Tp2 | Pulse length (msec) | 50 | 50 | 50 |
|  | Pulse interval (msec) | 50 | 50 | 50 |
|  | Number of pulses of each Tp (times) | Tp1: 5, Tp2: 5 | Tp1: 5, Tp2: 5 | Tp1: 5, Tp2: 5 |
|  | Decay rate (%) | 40 | 40 | 40 |
|  | Polarity | Tp1: +, Tp2: − | Tp1: +, Tp2: − | Tp1: +, Tp2: − |
|  | Presence or absence of transfer of exogenous compound | Present | Present | Present |

[Test Example 2 (Investigation Example)] "Investigation of Conditions for Poring Pulse"

An investigation was made of electric conditions for the poring pulse in the application of square-wave electric pulses. It should be noted that the investigation of the electric conditions was performed using cultured cells as samples instead of precious zygotes.

(1) "Preparation of Cell Solution"

Hela cells (adherent cells of an established cell line of human cervical cancer cells) were cultured, and after the removal of liquid medium, were washed with a 0.02% EDTA-PBS solution two or more times, and trypsin treatment was performed to detach cells in an adherent state. After the confirmation that the cells were detached, ES liquid medium (free of serum and an antibiotic, manufactured by Nissui Pharmaceutical Co., Ltd.) was added. Centrifugation was performed and the supernatant was discarded to remove trypsin. After that, the cells were resuspended in ES liquid medium.

50 μL of the cell suspension was collected and the number of cells was counted with a hemocytometer. After that, centrifugation (1,000 rpm, 5 min) was performed again and the remaining supernatant was discarded. The collected cells were resuspended by the addition of ES liquid medium to prepare a cell solution.

(2) "Preparation of DNA Solution"

A pCMV-EGFP plasmid was amplified using *Escherichia coli*, and plasmid DNA was prepared using a plasmid extraction kit.

(3) "Electric Pulse Treatment"

In a 2 mL Eppendorf tube, the cell solution and the DNA solution were thoroughly mixed at normal temperature without foaming to prepare a suspension having a final cell concentration of $1 \times 10^7$ cells/mL and a final DNA concentration of 100 μg/mL. 100 μL of the solution was charged into a 2 mm gap cuvette (EC-002S NEPA cuvette electrode having a capacity of from 40 μL to 400 μL, Nepa Gene Co., Ltd.).

The cuvette was mounted to a cuvette electrode chamber (CU500, Nepa Gene Co., Ltd.) of an electric pulse-generating device (NEPA21 (trademark), Nepa Gene Co., Ltd.) capable of generating square-wave electric pulses, and electric pulse treatment was performed based on the multiple pulse electroporation method involving sequentially applying two kinds of square-wave electric pulses, i.e., the poring pulse (Pp) and the transfer pulse (Tp). The respective conditions for the electric pulses were set to the conditions shown in Table 2. It should be noted that the series of operations was performed under a room temperature condition in order to prevent a water droplet from adhering.

(4) "Evaluation of Transformation Efficiency"

Within 1 minute after the electric pulse treatment, MEM medium containing serum and an antibiotic was injected into the cuvette, and the whole amount of the cell liquid was collected with a syringe, added into a culture plate charged with MEM medium containing serum and an antibiotic, and cultured under the conditions of 37° C. and a carbon dioxide concentration of 5%.

In addition, as a control, cells not subjected to electric pulse treatment were similarly cultured.

After 24 hours from the electric pulse treatment (before the expression peak of GFP but before the occurrence of cell proliferation), trypan blue staining was performed and the number of cells was counted under an optical microscope in a bright field and was compared to that of the control to calculate a survival rate.

In addition, the number of cells expressing GFP was counted using a fluorescence microscope (excitation light: 490 nm, detected fluorescence: 510 nm) and was compared to the number counted in the bright field to calculate a transfer rate.

Transformation efficiency under each electric pulse condition was evaluated based on the calculated values of the survival rate and the transfer rate.

(5) "Results"

As shown by the results of Table 2-A, it was shown that, under the condition that the pulse length of the poring pulse was adjusted to adjust the total energy amount to be nearly constant, when the voltage of the poring pulse was applied in the range of from 250 V/cm to 750 V/cm, the transfer rate showed a high value in samples to which a voltage of 375 V/cm or more had been applied (Tests 2A-1 to 2A-5). In addition, it was shown that the value of the survival rate was also high in such electric condition range.

In addition, as shown by the results of Table 2-B, it was shown that, under the condition that the pulse length of the poring pulse was adjusted to adjust the total energy amount to be nearly constant, when the voltage of the poring pulse was applied in the wide range of from 500 V/cm to 4,500 V/cm, the value of the survival rate of cells after the electric treatment was dramatically high in any of the samples (Tests 2B-1 to 2B-9). It was shown that the value of the transfer rate was also remarkably high in such electric condition range. It should be noted that, in particular, it was shown that the survival rate was satisfactory even under the extremely high voltage condition of 4,500 V/cm.

From those findings, it was suggested that, in order to obtain high results for both the survival rate and the transfer efficiency by gene transfer with square-wave electric pulses, it was suitable to set the lower limit of the voltage value of the poring pulse to 375 V/cm or more. It was also suggested that, as long as the energy amount of the poring pulse fell within a predetermined range, the upper limit of the voltage value of the poring pulse did not particularly affect the survival rate and the transfer efficiency.

TABLE 2-A

| | Test 2A-1 | Test 2A-2 | Test 2A-3 | Test 2A-4 | Test 2A-5 |
|---|---|---|---|---|---|
| Interelectrode gap (mm) | 2 | 2 | 2 | 2 | 2 |
| Liquid volume (μL) | 100 | 100 | 100 | 100 | 100 |
| Impedance value (Ω) | 34 | 41 | 34 | 36 | 38 |
| Pp Voltage (V/cm) | 250 | 375 | 500 | 625 | 750 |
| Pulse length (msec) | 35 | 15 | 8 | 5 | 4 |
| Pulse interval (msec) | — | — | — | — | — |
| Number of pulses (times) | 1 | 1 | 1 | 1 | 1 |
| Decay rate (%) | — | — | — | — | — |
| Energy of first one pulse (J/100 μL) | 2.574 | 2.058 | 2.353 | 2.170 | 2.368 |
| Total energy (J/100 μL) | 2.574 | 2.058 | 2.353 | 2.170 | 2.368 |
| Pulse interval (msec) | 50 | 50 | 50 | 50 | 50 |
| Tp Voltage (V/cm) | 100 | 100 | 100 | 100 | 100 |
| Pulse length (msec) | 50 | 50 | 50 | 50 | 50 |
| Pulse interval (msec) | 50 | 50 | 50 | 50 | 50 |
| Number of pulses (times) | 10 | 10 | 10 | 10 | 10 |
| Decay rate (%) | 0 | 0 | 0 | 0 | 0 |
| Polarity | Tp: + | Tp: + | Tp: + | Tp: + | Tp: + |
| Energy of first one pulse (J/100 μL) | 0.588 | 0.488 | 0.588 | 0.556 | 0.526 |
| Total energy (J/100 μL) | 5.882 | 4.878 | 5.882 | 5.556 | 5.263 |
| Survival rate (%) | 95 | 90 | 90 | 70 | 70 |
| Transfer rate (%) | 0 | 45 | 93 | 94 | 96 |

TABLE 2-B

| | Test 2B-1 | Test 2B-2 | Test 2B-3 | Test B-4 | Test 2B-5 | Test 2B-6 | Test 2B-7 | Test 2B-8 | Test 2B-9 |
|---|---|---|---|---|---|---|---|---|---|
| Interelectrode gap (mm) | 2 | 2 | 2 | 2 | 2 | 2 | 2 | 2 | 2 |
| Liquid volume (μL) | 100 | 100 | 100 | 100 | 100 | 100 | 100 | 100 | 100 |
| Impedance value (Ω) | 42 | 47 | 41 | 39 | 40 | 39 | 45 | 41 | 41 |
| Pp Voltage (V/cm) | 500 | 625 | 750 | 875 | 1,000 | 1,500 | 2,500 | 3,750 | 4,500 |

TABLE 2-B-continued

|  |  | Test 2B-1 | Test 2B-2 | Test 2B-3 | Test B-4 | Test 2B-5 | Test 2B-6 | Test 2B-7 | Test 2B-8 | Test 2B-9 |
|---|---|---|---|---|---|---|---|---|---|---|
|  | Pulse length (msec) | 8 | 5 | 3.5 | 2.5 | 2 | 0.9 | 0.3 | 0.15 | 0.1 |
|  | Pulse interval (msec) | — | — | — | — | — | — | — | — | — |
|  | Number of pulses (times) | 1 | 1 | 1 | 1 | 1 | 1 | 1 | 1 | 1 |
|  | Decay rate (%) | — | — | — | — | — | — | — | — | — |
|  | Energy of first one pulse (J/100 μL) | 1.905 | 1.662 | 1.921 | 1.963 | 2.000 | 2.077 | 1.667 | 2.058 | 1.976 |
|  | Total energy (J/100 μL) | 1.905 | 1.662 | 1.921 | 1.963 | 2.000 | 2.077 | 1.667 | 2.058 | 1.976 |
| Pulse interval (msec) |  | 50 | 50 | 50 | 50 | 50 | 50 | 50 | 50 | 50 |
| Tp | Voltage (V/cm) | 100 | 100 | 100 | 100 | 100 | 100 | 100 | 100 | 100 |
|  | Pulse length (msec) | 50 | 50 | 50 | 50 | 50 | 50 | 50 | 50 | 50 |
|  | Pulse interval (msec) | 50 | 50 | 50 | 50 | 50 | 50 | 50 | 50 | 50 |
|  | Number of pulses (times) | 10 | 10 | 10 | 10 | 10 | 10 | 10 | 10 | 10 |
|  | Decay rate (%) | 0 | 0 | 0 | 0 | 0 | 0 | 0 | 0 | 0 |
|  | Polarity | Tp: + | Tp: + | Tp: + | Tp: + | Tp: + | Tp: + | Tp: + | Tp: + | Tp: + |
|  | Energy of first one pulse (J/100 μL) | 0.476 | 0.426 | 0.488 | 0.513 | 0.500 | 0.513 | 0.444 | 0.488 | 0.488 |
|  | Total energy (J/100 μL) | 4.762 | 4.255 | 4.878 | 5.128 | 5.000 | 5.128 | 4.444 | 4.878 | 4.878 |
| Survival rate (%) |  | 90 | 80 | 70 | 70 | 70 | 70 | 70 | 70 | 80 |
| Transfer rate (%) |  | 86 | 95 | 97 | 95 | 95 | 96 | 93 | 96 | 91 |

[Test Example 3 (Investigation Example)]
"Investigation of Conditions for Poring Pulse"

An investigation was made of electric conditions for the poring pulse in the application of square-wave electric pulses. It should be noted that the investigation of the electric conditions was performed using cultured cells as samples instead of precious zygotes.

(1) "Preparation of Cell Solution and DNA Solution"

A suspended solution of Hela cells was prepared in the same manner as in the method described in Test Example 2(1), and was used as a cell solution. In addition, a pCMV-EGFP plasmid solution was prepared in the same manner as in the method described in Test Example 2(2), and was used as a DNA solution.

(2) "Electric Pulse Treatment"

A cell/DNA suspension (Hela cells: $1 \times 10^7$ cells/mL, pCMV-EGFP: 100 μg/mL) was prepared and 100 μL of the solution was charged into a 2 mm gap cuvette in the same manner as in the method described in Test Example 2(3).

Electric pulse treatment was performed for each prepared sample under the electric conditions shown in Table 3. The equipment and basic operations used in this treatment were the same as in the method described in Test Example 2(3).

(3) "Evaluation of Transformation Efficiency"

A survival rate and transfer efficiency were calculated and transformation efficiency was evaluated in the same manner as in the method described in Test Example 2(4).

(4) "Results"

As shown by the results of Table 3-A, it was shown that, under the condition that the voltage of the poring pulse was adjusted to be constant, when the electric pulses were applied so that the total energy amount of the poring pulse was from 0.080 J/100 μL to 2.298 J/100 μL, the value of the transfer rate was dramatically high in samples to which the electric pulses had been applied so that the total energy amount was 0.286 J/100 μL or more (Tests 3A-3 to 3A-11). It was shown that the value of the survival rate was also high in such electric condition range. In addition, in particular, it was shown that the value of the transfer rate was as high as 70% or more in samples for which the total energy amount was 0.535 J/100 μL or more (Tests 3A-4 to 3A-11).

It should be noted that the values of the energy amount 'per pulse' and pulse length of the poring pulse did not correlate to any of the transfer rate and the survival rate.

In addition, as shown by the results of Table 3-B, it was shown that, under the condition that the voltage of the poring pulse was adjusted to be constant, when the electric pulses were applied so that the total energy amount of the poring pulse was from 2.5 J/100 μL to 7.317 J/100 μL, the value of the survival rate was high (Tests 3B-1 to 3B-3). It was shown that the value of the transfer rate was also remarkably high in such electric condition range. It should be noted that the survival rate was satisfactory even when the pulse having a high total energy amount of 7.317 J/100 μL was applied.

From those findings, it was suggested that, in order to obtain high results for both the survival rate and the transfer efficiency by gene transfer with square-wave electric pulses, it was suitable to set the lower limit of the 'total' energy amount (total energy amount) of the poring pulse to 0.286 J/100 μL or more, preferably 0.535 J/100 μL or more. It was also suggested that, when the upper limit thereof was set to 7.317 J/100 μL or less, the survival rate and the transfer rate were satisfactory.

TABLE 3-A

|  |  | Test 3A-1 | Test 3A-2 | Test 3A-3 | Test 3A-4 | Test 3A-5 | Test 3A-6 | Test 3A-7 | Test 3A-8 | Test 3A-9 | Test 3A-10 | Test 3A-11 |
|---|---|---|---|---|---|---|---|---|---|---|---|---|
| Interelectrode gap (mm) |  | 2 | 2 | 2 | 2 | 2 | 2 | 2 | 2 | 2 | 2 | 2 |
| Liquid volume (μL) |  | 100 | 100 | 100 | 100 | 100 | 100 | 100 | 100 | 100 | 100 | 100 |
| Impedance value (Ω) |  | 195 | 82 | 164 | 73 | 140 | 124 | 92 | 175 | 61 | 74 | 102 |
| Pp | Voltage (V/cm) | 625 | 625 | 625 | 625 | 625 | 625 | 625 | 625 | 625 | 625 | 625 |
|  | Pulse length (msec) | 0.1 | 0.1 | 1 | 0.5 | 5 | 2.5 | 1 | 5 | 2.5 | 1 | 5 |
|  | Pulse interval (msec) | 50 | 50 | 50 | 50 | 50 | 50 | 50 | 50 | 50 | 50 | 50 |

TABLE 3-A-continued

|  | | Test 3A-1 | Test 3A-2 | Test 3A-3 | Test 3A-4 | Test 3A-5 | Test 3A-6 | Test 3A-7 | Test 3A-8 | Test 3A-9 | Test 3A-10 | Test 3A-11 |
|---|---|---|---|---|---|---|---|---|---|---|---|---|
|  | Number of pulses (times) | 10 | 5 | 3 | 5 | 1 | 2 | 5 | 2 | 3 | 10 | 3 |
|  | Decay rate (%) | 0 | 0 | 0 | 0 | 0 | 0 | 0 | 0 | 0 | 0 | 0 |
|  | Energy of first one pulse (J/100 μL) | 0.008 | 0.019 | 0.095 | 0.107 | 0.558 | 0.315 | 0.170 | 0.446 | 0.640 | 0.211 | 0.766 |
|  | Total energy (J/100 μL) | 0.080 | 0.095 | 0.286 | 0.535 | 0.558 | 0.630 | 0.849 | 0.893 | 1.921 | 2.111 | 2.298 |
| Tp | Pulse interval (msec) | 50 | 50 | 50 | 50 | 50 | 50 | 50 | 50 | 50 | 50 | 50 |
|  | Voltage (V/cm) | 100 | 100 | 100 | 100 | 100 | 100 | 100 | 100 | 100 | 100 | 100 |
|  | Pulse length (msec) | 50 | 50 | 50 | 50 | 50 | 50 | 50 | 50 | 50 | 50 | 50 |
|  | Pulse interval (msec) | 50 | 50 | 50 | 50 | 50 | 50 | 50 | 50 | 50 | 50 | 50 |
|  | Number of pulses (times) | 1 | 1 | 1 | 1 | 1 | 1 | 1 | 1 | 1 | 1 | 1 |
|  | Decay rate (%) | — | — | — | — | — | — | — | — | — | — | — |
|  | Polarity | Tp: + | Tp: + | Tp: + | Tp: + | Tp: + | Tp: + | Tp: + | Tp: + | Tp: + | Tp: + | Tp: + |
|  | Energy of first one pulse (J/100 μL) | 0.103 | 0.244 | 0.122 | 0.274 | 0.143 | 0.161 | 0.217 | 0.114 | 0.328 | 0.270 | 0.196 |
|  | Total energy (J/100 μL) | 0.103 | 0.244 | 0.122 | 0.274 | 0.143 | 0.161 | 0.217 | 0.114 | 0.328 | 0.270 | 0.196 |
| Survival rate (%) | | 90 | 90 | 90 | 90 | 90 | 90 | 80 | 80 | 80 | 70 | 70 |
| Transfer rate (%) | | 0 | 5 | 51 | 73 | 72 | 76 | 87 | 92 | 95 | 94 | 96 |

TABLE 3-B

|  | | Test 3B-1 | Test 3B-2 | Test 3B-3 |
|---|---|---|---|---|
|  | Interelectrode gap (mm) | 2 | 2 | 2 |
|  | Liquid volume (μL) | 100 | 100 | 100 |
|  | Impedance value (Ω) | 40 | 47 | 41 |
| Pp | Voltage (V/cm) | 500 | 500 | 500 |
|  | Pulse length (msec) | 10 | 20 | 30 |
|  | Pulse interval (msec) | — | — | — |
|  | Number of pulses (times) | 1 | 1 | 1 |
|  | Decay rate (%) | — | — | — |
|  | Energy of first one pulse (J/100 μL) | 2.500 | 4.255 | 7.317 |
|  | Total energy (J/100 μL) | 2.500 | 4.255 | 7.317 |
|  | Pulse interval (msec) | 50 | 50 | 50 |
| Tp | Voltage (V/cm) | 100 | 100 | 100 |
|  | Pulse length (msec) | 50 | 50 | 50 |
|  | Pulse interval (msec) | 50 | 50 | 50 |
|  | Number of pulses (times) | 10 | 10 | 10 |
|  | Decay rate (%) | 0 | 0 | 0 |
|  | Polarity | Tp: + | Tp: + | Tp: + |
|  | Energy of first one pulse (J/100 μL) | 0.500 | 0.426 | 0.488 |
|  | Total energy (J/100 μL) | 5.000 | 4.255 | 4.878 |
| Survival rate (%) | | 90 | 90 | 50 |
| Transfer rate (%) | | 93 | 95 | 91 |

[Test Example 4 (Investigation Example)]
"Investigation of Conditions for Transfer Pulse"

An investigation was made of electric conditions for the transfer pulse in the application of square-wave electric pulses. It should be noted that the investigation of the electric conditions was performed using cultured cells as samples instead of precious zygotes.

(1) "Preparation of Cell Solution and DNA Solution"

A suspended solution of Hela cells was prepared in the same manner as in the method described in Test Example 2(1), and was used as a cell solution. In addition, a pCMV-EGFP plasmid solution was prepared in the same manner as in the method described in Test Example 2(2), and was used as a DNA solution.

(2) "Electric Pulse Treatment"

A cell/DNA suspension (Hela cells: $1 \times 10^7$ cells/mL, pCMV-EGFP: 100 μg/mL) was prepared and 100 μL of the solution was charged into a 2 mm gap cuvette in the same manner as in the method described in Test Example 2(3).

Electric pulse treatment was performed for each prepared sample under the electric conditions shown in Table 4. The equipment and basic operations used in this treatment were the same as in the method described in Test Example 2(3).

(3) "Evaluation of Transformation Efficiency"

A survival rate and transfer efficiency were calculated and transformation efficiency was evaluated in the same manner as in the method described in Test Example 2(4).

(4) "Results"

As shown by the results of Table 4-A, it was shown that the value of the survival rate was high in samples to which the electric pulses had been applied so that the transfer pulse energy amount per pulse was from 0.012 J/100 μL to 0.588 J/100 μL (Tests 4A-1 to 4A-4). It was shown that the value of the transfer rate was also high in such electric condition range. In addition, in particular, it was shown that the value of the survival rate was as high as 80% or more in samples for which the transfer pulse energy amount per pulse was 0.07 J/100 μL or more (Tests 4A-3 and 4A-4).

In addition, as shown by the results of Table 4-B, it was shown that the value of the survival rate was high also in samples to which the electric pulses had been applied so that the transfer pulse energy amount per pulse was from 0.135 J/100 μL to 3.571 J/100 μL (Tests 4B-1 to 4B-7). It was shown that the value of the transfer rate was also remarkably high in such electric condition range. In addition, in particular, it was shown that the value of the survival rate was as high as 80% or more in samples for which the transfer pulse energy amount per pulse was 0.679 J/100 μL or less (Tests 4B-1 to 4B-4).

It should be noted that, with regard to the transfer pulse, it was suggested that the upper limit value of the 'total' energy of the transfer pulse did not correlate to the survival rate because the survival rate was satisfactory even when the transfer pulse was applied with a total energy amount of an extremely high value of 35.714 J/100 μL.

From those findings, it was suggested that, in order to obtain high results for both the survival rate and the transfer efficiency by gene transfer with square-wave electric pulses, it was suitable to set the lower limit of the energy amount 'per pulse' of the transfer pulse to 0.012 J/100 μL or more. It was also suggested that, when the upper limit of the energy amount 'per pulse' was set to 3.571 J/100 μL or less, particularly 1.250 J/100 μL or less, or even 0.679 J/100 μL or less, the survival rate and the transfer rate were satisfactory.

TABLE 4-A

|  |  | Test 4A-1 | Test 4A-2 | Test 4A-3 | Test 4A-4 |
|---|---|---|---|---|---|
| Interelectrode gap (mm) | | 2 | 2 | 2 | 2 |
| Liquid volume (μL) | | 100 | 100 | 100 | 100 |
| Impedance value (Ω) | | 38 | 37 | 25 | 34 |
| Pp | Voltage (V/cm) | 625 | 625 | 625 | 625 |
| | Pulse length (msec) | 5 | 5 | 5 | 5 |
| | Pulse interval (msec) | — | — | — | — |
| | Number of pulses (times) | 1 | 1 | 1 | 1 |
| | Decay rate (%) | — | — | — | — |
| | Energy of first one pulse (J/100 μL) | 2.056 | 2.111 | 2.232 | 2.298 |
| | Total energy (J/100 μL) | 2.056 | 2.111 | 2.232 | 2.298 |
| | Pulse interval (msec) | 50 | 50 | 50 | 50 |
| Tp | Voltage (V/cm) | 15 | 25 | 35 | 100 |
| | Pulse length (msec) | 50 | 50 | 50 | 50 |
| | Pulse interval (msec) | 50 | 50 | 50 | 50 |
| | Number of pulses (times) | 10 | 10 | 10 | 10 |
| | Decay rate (%) | 0 | 0 | 0 | 0 |
| | Polarity | Tp: + | Tp: + | Tp: + | Tp: + |
| | Energy of first one pulse (J/100 μL) | 0.012 | 0.034 | 0.070 | 0.588 |
| | Total energy (J/100 μL) | 0.118 | 0.338 | 0.700 | 5.882 |
| | Survival rate (%) | 60 | 60 | 80 | 90 |
| | Transfer rate (%) | 83 | 83 | 85 | 86 |

TABLE 4-B

|  | Test 4B-1 | Test 4B-2 | Test 4B-3 | Test 4B-4 | Test 4B-5 | Test 4B-6 | Test 4B-7 |
|---|---|---|---|---|---|---|---|
| Interelectrode gap (mm) | 2 | 2 | 2 | 2 | 2 | 2 | 2 |
| Liquid volume (μL) | 100 | 100 | 100 | 100 | 100 | 100 | 100 |
| Impedance value (Ω) | 37 | 36 | 36 | 46 | 36 | 35 | 35 |
| Pp Voltage (V/cm) | 625 | 625 | 625 | 625 | 625 | 625 | 625 |
| Pulse length (msec) | 5 | 5 | 5 | 5 | 5 | 5 | 5 |
| Pulse interval (msec) | — | — | — | — | — | — | — |
| Number of pulses (times) | 1 | 1 | 1 | 1 | 1 | 1 | 1 |
| Decay rate (%) | — | — | — | — | — | — | — |
| Energy of first one pulse (J/100 μL) | 2.111 | 2.170 | 2.170 | 1.698 | 2.170 | 2.232 | 2.232 |
| Total energy (J/100 μL) | 2.111 | 2.170 | 2.170 | 1.698 | 2.170 | 2.232 | 2.232 |
| Pulse interval (msec) | 50 | 50 | 50 | 50 | 50 | 50 | 50 |
| Tp Voltage (V/cm) | 50 | 75 | 100 | 125 | 150 | 200 | 250 |
| Pulse length (msec) | 50 | 50 | 50 | 50 | 50 | 50 | 50 |
| Pulse interval (msec) | 50 | 50 | 50 | 50 | 50 | 50 | 50 |
| Number of pulses (times) | 10 | 10 | 10 | 10 | 10 | 10 | 10 |
| Decay rate (%) | 0 | 0 | 0 | 0 | 0 | 0 | 0 |
| Polarity | Tp: + | Tp: + | Tp: + | Tp: + | Tp: + | Tp: + | Tp: + |
| Energy of first one pulse (J/100 μL) | 0.135 | 0.313 | 0.556 | 0.679 | 1.250 | 2.286 | 3.571 |
| Total energy (J/100 μL) | 1.351 | 3.125 | 5.556 | 6.793 | 12.500 | 22.857 | 35.714 |
| Survival rate (%) | 80 | 90 | 90 | 80 | 65 | 50 | 50 |
| Transfer rate (%) | 88 | 91 | 91 | 89 | 94 | 95 | 92 |

[Test Example 5 (Example)] "Test for Creation of Recombinant by ZFN mRNA Transfer"

An investigation was made of whether or not a recombinant was able to be created through the transfer of ZFN-encoding mRNA into a pronuclear-stage zygote with an intact zona pellucida by performing electroporation based on the square-wave three-step method. It should be noted that Il2rg gene present on the X chromosome was adopted as a target gene.

(1) "Preparation of mRNA"

A pair of ZFN plasmids (ZFN left and ZFN right) targeting rat interleukin-2 receptor γ chain gene (Il2rg: causative gene for immunodeficiency) was synthesized (Sigma Aldrich, St. Louis, Mo., USA). The pair of ZFNs was designed to bind to certain sequences near the second exon of the Il2rg gene (ZFN left: SEQ ID NO: 2, ZFN right: SEQ ID NO: 3) (see FIG. 6). It should be noted that the binding sequence of the ZFN left is a complementary strand sequence to the sequence of the Il2rg gene.

Each plasmid DNA having such construct was transferred into rat fibroblasts, and a Surveyor assay (Sigma Aldrich, St. Louis, Mo., USA) was performed to confirm that a mutation was introduced into the Il2rg gene by the sequence-specific nuclease activity of the ZFN.

Next, the plasmids were subjected to in vitro transcription using a MessageMax™ T7 mRNA transcription kit (Cambio, Cambridge, UK), and then subjected to polyadenylation treatment for the 3' end using an A-Plus™ Poly(A) polymerase tailing kit (Epicentre Biotechnologies, Madison, Wis., USA).

Each resultant mRNA (about 1 kb) was purified using a MEGAClear™ kit (Life Technologies Co., Carlsbad, Calif., USA). The mRNAs were dissolved in PBS at a concentration of 40 ng/μL each (80 ng/μL in total) to prepare a ZFN mRNA solution targeting the Il2rg gene.

(2) "Collection of Zygote"

Pronuclear-stage zygotes of rats of the F344/Stm strain were collected and stored in modified Krebs-Ringer solution in the same manner as in the method described in Test Example 1(1).

(3) "Electric Pulse Treatment"

Between petri dish platinum plate electrodes (CUY520P5, 5 mm gap, L10×W5×H5 mmm, manufactured by Nepa Gene Co., Ltd.) on a glass chamber, 100 μL of phosphate buffered saline (PBS) containing the mRNAs at 40 ng/μL each was injected, and the collected pronuclear-stage zygotes were placed at rest in a line between the phosphate buffer saline-charged metal plate electrodes (see FIG. 3(A)). In this case, the pronuclear-stage zygotes were used while keeping the state at the time of being collected without being subjected to zona pellucida-removing and thinning treatment.

To the metal plate, an electric pulse-generating device (NEPA21 (trademark), manufactured by Nepa Gene Co., Ltd.) capable of generating square-wave electric pulses was connected (see FIG. 3(B)), and electric pulse treatment was performed based on the electroporation method involving using multiple pulses by the three steps of sequentially applying three kinds of square-wave electric pulses, i.e., the poring pulse (Pp), the transfer pulse 1 (Tp1), and the transfer pulse (Tp2) (see FIG. 1 and FIG. 2). The respective conditions for the electric pulses were set to the conditions shown in Table 5-A. It should be noted that the series of operations was performed under a room temperature condition in order to prevent a water droplet from adhering.

Meanwhile, as a control, the respective mRNAs were transferred into zygotes by microinjection (microinjection method) involving using a micromanipulator. It should be noted that the injection operation was performed in accordance with an ordinary method, and about 2 pL of PBS containing the mRNAs at 10 ng/μL each was transferred.

(4) "Transplantation of Zygote"

The zygotes after the transfer treatment were cultured into 2-cell stage embryos in modified Krebs-Ringer solution under the conditions of 37° C., 5% $CO_2$, and 95% air. The number of the 2-cell stage embryos was counted, and the ratio (%) of the number of 2-cell stage embryos to the number of tested eggs was calculated.

The resultant 2-cell stage embryos were transplanted into the oviducts of pseudopregnant female rats (individual allowed to mate with vascectomised males on the previous day) of the Jcl:Wistar strain (CLEA Japan Inc.). Offspring were obtained through spontaneous delivery 21 days after the transplantation. The ratio (%) of the number of offspring to the number of tested eggs was calculated.

(5) "Analysis for Gene Mutation of Offspring"

Blood was collected from grown offspring, and was allowed to adhere to an FTA card and stored. Genomic DNA was extracted from the FTA card (manufactured by GE Healthcare Life Sciences), and regions interposing therebetween the mutation site designed on the Il2rg gene were amplified by a PCR reaction. The resultant PCR product was subjected to sequence analysis to analyze the presence or absence of the Il2rg gene mutation in the genomic DNA of the offspring. The ratio of mutant offspring individuals to all individuals of the offspring was calculated.

(6) "Results"

Figure 5:
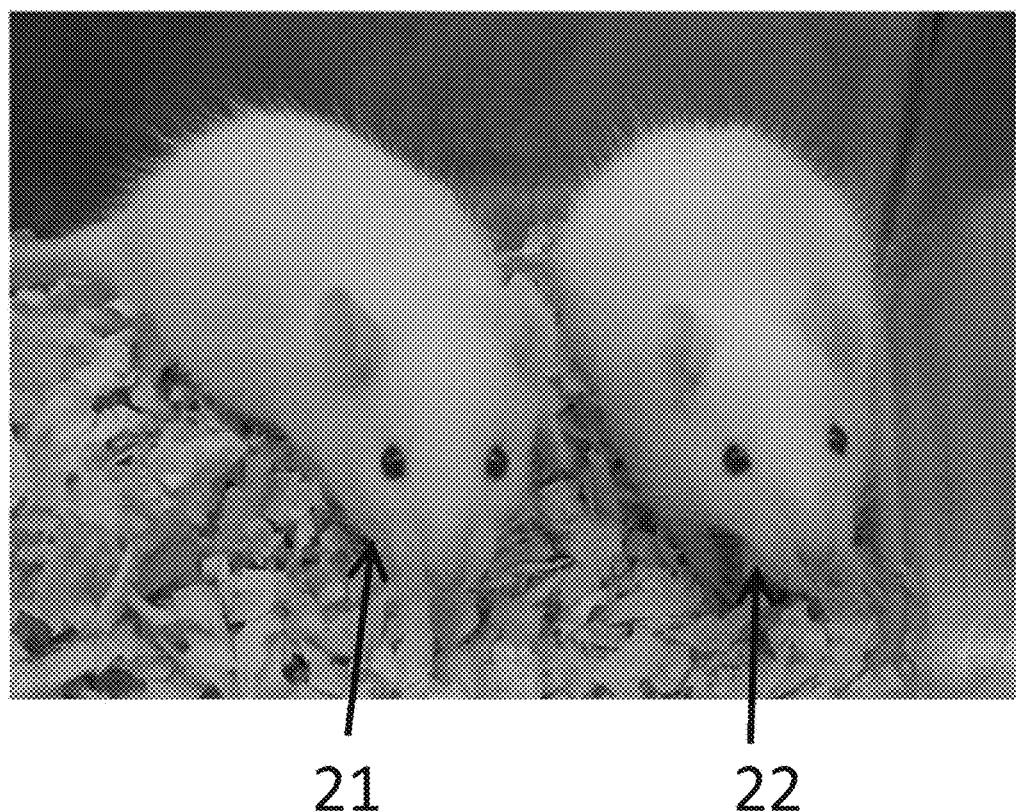
FIG. 5 is a photographic image taken of a knockout rat created by transferring ZFN mRNA targeting Il2rg gene in Test Example 5. On the left, an Il2rg gene knockout rat is shown. On the right, a wild-type rat (F344/Stm strain) is shown.

As shown by the results of Table 5-B, it was shown that genetically modified mice (Il2rg gene-knockout rats) utilizing the sequence-specific nuclease activity of ZFN were able to be efficiently produced through efficient transfer of ZFN-encoding mRNA into pronuclear-stage zygotes with an intact zona pellucida by performing electric pulse treatment based on the square-wave three-step method involving adjusting the total energy amount of the poring pulse to from 0.298 J/100 μL to 1.062 J/100 μL (see FIG. 5).

Specifically, it was shown that the survival rate of the zygotes (2-cell stage embryo yield, offspring yield) after the electric pulse treatment showed efficiency comparable to or higher than that in the microinjection method (Tests 5-1 to 5-3). Particularly when the total energy amount of the poring pulse was adjusted to from 0.298 J/100 μL to 0.629 J/100 μL, the value of the yield of the offspring (survival rate) was from 2.4 times to 3.1 times as high as that in the microinjection method (Tests 5-1 and 5-2).

The reason for the high survival rate was presumed to be as follows: in addition to not performing zona pellucida-removing and thinning treatment, the total energy amount of the poring pulse falling within a suitable range reduced damage to the zygotes.

In addition, the gene mutation rate of the resultant offspring showed efficiency comparable to or higher than that in the microinjection method. Particularly when the total energy amount of the poring pulse was adjusted to from 0.629 J/100 μL to 1.062 J/100 μL, the value of the mutation rate was about 2.2 times as high as that in the microinjection method.

TABLE 5-A

|   |   | Test 5-1 | Test 5-2 | Test 5-3 |
|---|---|---|---|---|
|   | Interelecurode gap (mm) | 5 | 5 | 5 |
|   | Liquid volume (μL) | 100 | 100 | 100 |
|   | Impedance value (Ω) | 343 | 348 | 353 |
| Pp | Voltage (V/cm) | 450 | 450 | 450 |
|   | Pulse length (msec) | 0.5 | 1.5 | 2.5 |
|   | Pulse interval (msec) | 50 | 50 | 50 |
|   | Number of pulses (times) | 4 | 4 | 4 |
|   | Decay rate (%) | 10 | 10 | 10 |
|   | Energy of first one pulse (J/100 μL) | 0.070 | 0.205 | 0.340 |
|   | Total energy (J/100 μL) | 0.298 | 0.629 | 1.062 |
|   | Pulse interval (msec) | 50 | 50 | 50 |
| Tp1 | Voltage (V/cm) | 40 | 40 | 40 |
| Tp2 | Pulse length (msec) | 50 | 50 | 50 |
|   | Pulse interval (msec) | 50 | 50 | 50 |
|   | Number of pulses of each Tp (times) | Tp1: 5, Tp2: 5 | Tp1: 5, Tp2: 5 | Tp1: 5, Tp2: 5 |
|   | Decay rate (%) | 40 | 40 | 40 |
|   | Polarity | Tp1: +, Tp2: − | Tp1: +, Tp2: − | Tp1: +, Tp2: − |
|   | Energy of first one pulse (J/100 μL) | 0.048 | 0.049 | 0.050 |
|   | Total energy of Tp1 (J/100 μL) | 0.152 | 0.160 | 0.164 |
|   | Total energy of Tp2 (J/100 μL) | 0.152 | 0.160 | 0.164 |

TABLE 5-B

|   | Test 5-1 | Test 5-2 | Test 5-3 | Control (micro-injection) |
|---|---|---|---|---|
| Transferred substance | ZFN mRNA (40 ng/mL each) | ZFN mRNA (40 ng/mL each) | ZFN A mRNA (40 ng/mL each) | ZFN mRNA (40 ng/mL each) |
| Total energy of Pp (J/100 μL) | 0.298 | 0.629 | 1.062 | — |
| 2-Cell stage embryo yield (2-Cell stage embryos/zygotes) | 95% (58/61) | 91% (57/63) | 24% (16/66) | 44% (41/93) |
| Offspring yield (Offspring/zygotes) | 31% (19/61) | 24% (15/63) | 6% (4/66) | 10% (9/93) |
| Gene mutation rate of offspring (Mutant offspring/all offspring) | 37% (7/19) | 73% (11/15) | 75% (3/4) | 33% (3/9) |

[Test Example 6 (Example)] "Test for Creation of Recombinant by TALEN mRNA Transfer"

An investigation was made of whether or not a recombinant was able to be created through the transfer of TALEN-encoding mRNA into a pronuclear-stage zygote with an intact zona pellucida by performing electroporation based on the square-wave three-step method. It should be noted that Il2rg gene present on the X chromosome was adopted as a target gene.

(1) "Preparation of mRNA"

A pair of TALEN plasmids (TALEN left and TALEN right) encoding rat interleukin-2 receptor γ chain gene (Il2rg: causative gene for immunodeficiency) was synthesized. The pair of TALENs was designed to bind to certain sequences in the second exon of the Il2rg gene (TALEN left: SEQ ID NO: 5, TALEN right: SEQ ID NO: 6) (see FIG. 7). It should be noted that the binding sequence of the TALEN right is a complementary strand sequence to the sequence of the Il2rg gene.

Each plasmid DNA having such construct was transferred into rat fibroblasts, and a Surveyor assay (Sigma Aldrich, St. Louis, Mo., USA) was performed to confirm that a mutation was introduced into the Il2rg gene by the sequence-specific nuclease activity of the TALEN.

Next, the plasmids were subjected to in vitro transcription using a MessageMax™ T7 mRNA transcription kit (Cambio, Cambridge, UK), and then subjected to polyadenylation treatment for the 3' end using an A-Plus™ Poly(A) polymerase tailing kit (Epicentre Biotechnologies, Madison, Wis., USA).

Each resultant mRNA (about 3 kb) was purified using a MEGAClear™ kit (Life Technologies Co., Carlsbad, Calif., USA). The mRNAs were dissolved in PBS at a concentration of 40 ng/µL each (80 ng/µL in total) to prepare a TALEN mRNA solution targeting the Il2rg gene.

(2) "Collection of Zygote"

Pronuclear-stage zygotes of rats of the F344/Stm strain were collected and stored in modified Krebs-Ringer solution in the same manner as in the method described in Test Example 1(1).

(3) "Electric Pulse Treatment"

In the same manner as in the method described in Test Example 5(3), between petri dish platinum plate electrodes on a glass chamber, 100 µL of phosphate buffered saline (PBS) containing the mRNAs at 40 ng/µL each was injected, and the collected pronuclear-stage zygotes were placed at rest in a line between the phosphate buffer saline-charged metal plate electrodes. In this case, the pronuclear-stage zygotes were used while keeping the state at the time of being collected without being subjected to zona pellucida-removing and thinning treatment.

To the metal plate, an electric pulse-generating device capable of generating square-wave electric pulses was connected, and electric pulse treatment was performed with the total energy amount of the poring pulse shown in Table 6. In addition, the equipment, basic operations, and other electric conditions used in this treatment were the same as in the method described in Test Example 5(3).

(4) "Transplantation of Zygote"

The ratio (%) of the number of 2-cell stage embryos to the number of tested eggs and the ratio (%) of the number of offspring to the number of tested eggs were calculated in the same manner as in the method described in Test Example 5(4). After that, the resultant 2-cell stage embryos were transplanted into the oviducts of pseudopregnant females and offspring were obtained through spontaneous delivery. The ratio (%) of the number of offspring to the number of tested eggs was calculated. It should be noted that the basic operations of this treatment were performed in the same manner as in the method described in Test Example 5(4).

(5) "Analysis for Gene Mutation of Offspring"

The ratio of Il2rg gene mutant individuals to all individuals of the offspring was calculated in the same manner as in the method described in Test Example 5(5). It should be noted that the basic operations of this analysis were performed in the same manner as in the method described in Test Example 5(5).

(6) "Results"

As shown by the results of Table 6, it was shown that genetically modified rats utilizing the sequence-specific nuclease activity of TALEN were able to be efficiently produced through efficient transfer of TALEN-encoding mRNA into pronuclear-stage zygotes with an intact zona pellucida by performing electric pulse treatment based on the square-wave three-step method involving adjusting the total energy amount of the poring pulse to from 0.629 J/100 µL to 1.062 J/100 µL.

Specifically, it was shown that the value of the survival rate of the zygotes after the electric pulse treatment (2-cell stage embryo yield, offspring yield) became high (Tests 6-1 and 6-2). In particular, when the total energy amount of the poring pulse was adjusted to 0.629 J/100 µL, an extremely large number, i.e., about a half (44%), of the zygotes were grown into offspring (Test 6-1).

It was also shown that an individual having a gene mutation in the target sequence was obtained from the resultant offspring (Tests 6-1 and 6-2). In particular, it was shown that, when the total energy amount of the poring pulse was adjusted to 1.062 J/100 µL, a high mutation rate was obtained (Test 6-2).

It should be noted that the value of the gene mutation rate of the offspring obtained by transferring the TALEN mRNA was lower than that in the example of the transfer of the ZFNs mRNA in Example 5. This was presumably because the mRNA for the transfer of TALEN was long (about 3 times the ZFN mRNA) and hence hardly migrated into the cytoplasm.

TABLE 6

|  | Test 6-1 | Test 6-2 |
| --- | --- | --- |
| Transferred substance | TALEN mRNA (40 ng/mL each) | TALEN mRNA (40 ng/mL each) |
| Total energy of Pp (J/100 µL) | 0.629 | 1.062 |
| 2-Cell stage embryo yield (2-Cell stage embryos/zygotes) | 97% (55/57) | 98% (56/57) |
| Offspring yield (Offspring/zygotes) | 44% (44/57) | 30% (17/57) |
| Gene mutation rate of offspring (Mutant offspring/all offspring) | 4% (1/25) | 18% (3/17) |

[Test Example 7 (Example)] "Test for Creation of Recombinant Utilizing CRISPR-Cas9 System"

An investigation was made of whether or not a recombinant was able to be created through the transfer of Cas9 mRNA and guide RNA for a CRISPR system into a pronuclear-stage zygote with an intact zona pellucida by performing electroporation based on the square-wave three-step method. It should be noted that a tyrosinase gene was adopted as a target gene.

(1) "Preparation of RNA"

Guide RNA targeting rat tyrosinase gene (Thy: involved in melanin synthesis, its deletion causing an albino) was prepared by oligo synthesis. 20 bp on the 5' side of the guide RNA was designed to bind to a complementary strand of a target sequence (SEQ ID NO: 7) on the Thy gene (see FIG. 8). In addition, the 3' side of the guide RNA is a sequence (SEQ ID NO: 8: crRNA:tracrRNA) which forms a three-dimensional structure to specifically bind to a Cas9 nuclease.

An expression vector having incorporated therein the guide RNA was transcribed using a MEGAshortscript™ T7 kit (Life Technologies Co., Carlsbad, Calif., USA). In addition, an expression vector having incorporated therein the Cas9 nuclease (SpCas9) was subjected to in vitro transcription using a MessageMax™ T7 mRNA transcription kit (Cambio, Cambridge, UK), and then the 3' end of the resultant RNA was subjected to polyadenylation treatment using an A-Plus™ Poly(A) polymerase tailing kit (Epicentre Biotechnologies, Madison, Wis., USA).

The resultant guide RNA and Cas9 mRNA were purified using a MEGAClear™ kit (Life Technologies Co., Carlsbad, Calif., USA).

The resultant guide RNA and Cas9 mRNA were dissolved in PBS so as to have concentrations of 192 ng/μL and 312 ng/μL, respectively. Thus, an RNA solution for the CRISPR-Cas9 system targeting the Thy gene was prepared.

(2) "Collection of Zygote"

Pronuclear-stage zygotes of rats of the DA/Slc strain were collected and stored in modified Krebs-Ringer solution. The basic operations of this treatment were performed in the same manner as in the method described in Test Example 1(1).

(3) "Electric Pulse Treatment"

In the same manner as in the method described in Test Example 5(3), between petri dish platinum plate electrodes on a glass chamber, 100 μL of phosphate buffered saline (PBS) containing the RNAs (192 ng/μL of guide RNA and 312 ng/μL of Cas9 mRNA) was injected, and the collected pronuclear-stage zygotes were placed at rest in a line between the phosphate buffer saline-charged metal plate electrodes. In this case, the pronuclear-stage zygotes were used while keeping the state at the time of being collected without being subjected to zona pellucida-removing and thinning treatment.

To the metal plate, an electric pulse-generating device capable of generating square-wave electric pulses was connected, and electric pulse treatment was performed with the total energy amount of the poring pulse shown in Table 7. In addition, the equipment, basic operations, and other electric conditions used in this treatment were the same as in the method described in Test Example 5(3).

(4) "Transplantation of Zygote"

The ratio (%) of the number of 2-cell stage embryos to the number of tested eggs and the ratio (%) of the number of offspring to the number of tested eggs were calculated in the same manner as in the method described in Test Example 5(4).

(5) "Analysis for Gene Mutation of Embryo"

The ratio of the Thy gene mutant individuals to all individuals of the 2-cell stage embryos was calculated. It should be noted that the basic operations of this analysis were performed in the same manner as in the method described in Test Example 5(5).

(6) "Results"

As shown by the results of Table 7, it was shown that an early embryo having a gene mutation in the target sequence was obtained through the transfer of guide RNA and Cas9 mRNA into a pronuclear-stage zygote with an intact zona pellucida by performing electric pulse treatment based on the square-wave three-step method involving adjusting the total energy amount of the poring pulse to 1.062 J/100 μL (Test 7-1).

From the results, it was suggested that a genetically modified rat was able to be produced by utilizing the electroporation method and the CRISPR-Cas9 system.

TABLE 7

|  | Test 7-1 |
| --- | --- |
| Transferred substance | Guide RNA (192 ng/μL) |
|  | Cas9 mRNA (312 ng/μL) |
| Total energy of Pp (J/100 μL) | 1.062 |
| Gene mutation rate of embryos (Mutant embryos/all embryos) | 10% (1/10) |

[Test Example 8 (Example)] "Test for Passage of Genetic Trait"

Whether or not the genetic trait transferred into the Il2rg gene mutant created in the foregoing was passed on to the next generation was confirmed.

(1) "Germ Line Transmission Analysis"

Screening was performed for Il2rg gene mutant rats of the genotype shown in Table 8 (Il2rg gene mutant individuals created through the transfer of ZFN mRNA in Test Example 5(4)). Now, in the table, 'G0Δ' or 'F1Δ' represents the presence of a mutation in the Il2rg gene on an X chromosome. In addition, a value on the right of Δ represents the number of deleted bases. In addition, '+' represents a normal X chromosome and 'Y' represents a Y chromosome.

The mutant individuals were each allowed to naturally mate with a wild type of the F344/Stm strain to provide offspring, and the ratio of gene mutant individuals was calculated. The presence or absence of a gene mutation was confirmed in the same manner as in the method described in Test Example 5(5).

(2) "Results"

As shown by the results of Table 8, in the offspring generation obtained by allowing a male Il2rg gene mutant individual, i.e., a mutant 8-1 (G0Δ13/Y) or a mutant 8-2 (G0Δ7/Y) to mate with a female wild type (+/+), all females were Il2rg gene mutants. In addition, all males in the offspring generation were wild types.

In addition, in the offspring generation obtained by allowing a female Il2rg gene mutant individual, i.e., a mutant 8-3 (F1Δ13/+) to mate with a male wild type (Y/+), about a half of both males and females were Il2rg gene mutants.

From the results, it was shown that the genetic trait (mutation on the genome) of the Il2rg gene mutant individual created through the transfer of ZFN mRNA was passed on to the offspring generation.

TABLE 8

|  | Parents' generation |  | Gene mutation rate of offspring generation (mutant offspring/offspring) | |
| --- | --- | --- | --- | --- |
|  | Mutant genotype | Backcrossed with | ♂ | ♀ |
| Test 8-1 | Mutant 8-1 G0Δ13/Y (♂) | +/+ (♀) | 0% (0/8) | 100% (5/5) |

TABLE 8-continued

| Parents' generation | | Gene mutation rate of offspring generation (mutant offspring/offspring) | |
|---|---|---|---|
| Mutant genotype | Backcrossed with | ♂ | ♀ |
| Test 8-2 Mutant 8-2 G0Δ7/Y (♂) | +/+ (♀) | 0% (0/7) | 100% (5/5) |
| Test 8-3 Mutant 8-3 F1Δ13/+ (♀) | +/Y (♂) | 60% (3/5) | 50% (3/6) |

[Test Example 9 (Comparative Example)] "Test for Transferring DNA into Zygote"

An investigation was made of whether or not a recombinant was able to be created through the transfer of plasmid DNA into a pronuclear-stage zygote with an intact zona pellucida by performing electroporation based on the square-wave three-step method.

(1) "Preparation of Plasmid DNA"

A plasmid solution of an EmGFP (Pc DNA6.2) plasmid (Invitrogen) was prepared and used as a DNA solution. The basic operations of plasmid preparation were performed in the same manner as in the method described in Test Example 2(2).

(2) "Electric Pulse Treatment"

In the same manner as in the method described in Test Example 5(3), between petri dish platinum plate electrodes on a glass chamber, 100 μL of phosphate buffered saline (PBS) containing the plasmid DNA at a concentration shown in Table 9 was injected, and the collected pronuclear-stage zygotes were placed at rest in a line between the phosphate buffer saline-charged metal plate electrodes. In this case, the pronuclear-stage zygotes were used while keeping the state at the time of being collected without being subjected to zona pellucida-removing and thinning treatment.

To the metal plate, an electric pulse-generating device capable of generating square-wave electric pulses was connected, and electric pulse treatment was performed with the total energy amount of the poring pulse shown in Table 9. In addition, the equipment, basic operations, and other electric conditions used in this treatment were the same as in the method described in Test Example 5(3).

(3) "Transplantation of Zygote"

The ratio (%) of the number of 2-cell stage embryos to the number of tested eggs and the ratio (%) of the number of offspring to the number of tested eggs were calculated in the same manner as in the method described in Test Example 5(4). It should be noted that the basic operations of this treatment were performed in the same manner as in the method described in Test Example 5(4).

(4) "Analysis for Gene Mutation of Offspring"

The offspring were shaved and irradiated with excitation light at 490 nm to examine whether or not their epidermal cells emitted fluorescence, to thereby calculate the ratio of GFP fluorescence-positive individuals to all individuals of the offspring.

(5) "Results"

As shown by the results of Table 9, in the case of using plasmid DNA as the molecular species of the transferred nucleic acid, even when the electric pulse treatment was performed under the optimum electric conditions determined in Test Examples above, no genetically modified individual was able to be produced.

From those results and the results of Test Examples 5 to 7, it was considered that it was suitable to use 'RNA' as the nucleic acid molecular species in order to genetically modify a 'zygote' with an intact zona pellucida by electroporation based on the square-wave three-step method.

TABLE 9

| | Test 9-1 | Test 9-2 | Test 9-3 |
|---|---|---|---|
| Transferred substance | Plasmid DNA (40 ng/μL) | Plasmid DNA (400 ng/μL) | Plasmid DNA (2,000 ng/μL) |
| Total energy of Pp (J/100 μL) | 0.629 | 0.629 | 0.629 |
| 2-Cell stage embryo yield (2-Cell stage embryos/zygotes) | 100% (20/20) | 88.2% (30/34) | 62.5% (25/40) |
| Offspring yield (Offspring/zygotes) | 50% (10/20) | 58.8% (20/34) | 0% (0/40) |
| Gene mutation rate of offspring (Mutant offspring/all offspring) | 0% (0/0) | 0% (0/0) | 0% (0/0) |

INDUSTRIAL APPLICABILITY

The gene modification technology of the present invention enables a genetically modified individual of a mammal to be created with high efficiency and good reproducibility without being limited to certain species of mammals in the utilization of the technology for modifying a gene having a target sequence on a genome (genome editing technology based on ZFN or the like).

Thus, the technology according to the present invention is expected to be a technology which significantly contributes to the analysis of a gene function or the elucidation of a disease mechanism.

It should be noted that the inventors of the present application have named the technology of the present invention "TAKE method" (the Technique for Animal Knockout system by Electroporation method).

REFERENCE SIGNS LIST

1: Electrode
2: Pronuclear-stage zygote
3: Egg-derived nucleus
4: Sperm-derived nucleus
5: Zona pellucida
6: Micropore formed with poring pulse
7: mRNA
11: Glass chamber provided with petri dish platinum plate electrodes
12: Petri dish platinum plate electrode
13: Stereoscopic microscope
14: Electric pulse-generating device
21: Il2rg gene knock-out rat
22: Wild-type rat (F344/Stm strain)
31: Binding sequence (complementary strand sequence) of ZFN left designed in Il2rg gene
32: Zinc Finger Proteins (sequence-specific DNA-binding domain)
33: FokI (restriction enzyme activity domain)
34: Binding sequence (gene sequence) of ZFN right designed in Il2rg gene
35: Zinc Finger Proteins (sequence-specific DNA-binding domain)

36: FokI (restriction enzyme activity domain)
41: Binding sequence (gene sequence) of TALEN left designed in Il2rg gene
42: Transcription activator-like effectors (sequence-specific DNA-binding domain)
43: FokI (restriction enzyme activity domain)
44: Binding sequence (complementary strand sequence) of TALEN right designed in Il2rg gene
45: Transcription activator-like effectors (sequence-specific DNA-binding domain)
46: FokI (restriction enzyme activity domain)
51: Genomic DNA of Thy gene
52: Recognition sequence for guide RNA of CRISPR-Cas9 system designed in Thy gene.
53: Protospacer adaptor motif (PAM)
54: Guide RNA (crRNA:tracrRNA)
55: Cas9 nuclease

The invention claimed is:

1. A method of modifying a gene in a pronuclear stage zygote of a non-human mammal, comprising: (a) immersing a pronuclear stage zygote of a non-human mammal with an intact zona pellucida into a solution containing an RNA molecule having a sequence specific for an arbitrary region of genomic DNA in the zygote, wherein the solution further contains an endonuclease that is capable of binding to and cleaving the arbitrary region of the genomic DNA in a sequence-specific manner; (b) applying a square-wave electric pulse having a voltage per pulse of 375 V/cm or more to the solution at least once so that the square-wave electric pulse has a total electric energy of from 0.2 J/100 µL to 7.5 J/100 µL; (c) applying a square-wave electric pulse having a voltage per pulse of 250 V/cm or less and an electric energy per pulse of from 0.01 J/100 µL to 3.6 J/100 µL to the solution two or more times; and (d) applying a square-wave electric pulse which is opposite in polarity to the electric pulse of step (c) and has a voltage per pulse of 250 V/cm or less and an electric energy per pulse of 0.01 J/100 µL to 3.6 J/100 µL to the solution two or more times, wherein the method results in the pronuclear stage zygote of the non-human mammal comprising a genetic modification in the arbitrary region of genomic DNA.

2. The method according to claim 1, wherein the RNA molecule having a sequence specific for an arbitrary region of genomic DNA comprises (1) mRNA encoding a protein having a sequence-specific DNA-binding domain, and a domain which exhibits restriction enzyme activity as a dimer with a restriction enzyme activity domain as defined in (2); and (2) mRNA encoding a protein having a sequence-specific DNA-binding domain which is a region in a vicinity of a genomic DNA region end to which the protein as defined in (1) binds and which binds to a complementary strand thereof, and a domain which exhibits restriction enzyme activity as a dimer with the restriction enzyme activity domain as defined in (1).

3. The method according to claim 1, wherein the RNA molecule having a sequence specific for an arbitrary region of genomic DNA comprises (1) guide RNA having a complementary sequence of an arbitrary base sequence of the genomic DNA, and a sequence which specifically binds to a protein as defined in (2); and (2) mRNA encoding a protein which exhibits endonuclease activity when specifically binding to the guide RNA as defined in the item (1).

4. The method according to claim 1, wherein the solution further contains mRNA encoding exonuclease 1 (Exo1).

5. The method according to claim 1, wherein the non-human mammal is a species belonging to an order Rodentia.

6. The method according to claim 1, wherein step (c) is performed five or more times and step (d) is performed five or more times.

7. The method according to claim 1, wherein the modification of the gene causes deletion or suppression of a function by disruption of the gene.

8. The method according to claim 1, wherein the non-human mammal is a primate.

9. The method according to claim 1, wherein the non-human mammal is a swine.

\* \* \* \* \*

SEQUENCE LISTING

```
<160> NUMBER OF SEQ ID NOS: 8

<210> SEQ ID NO 1
<211> LENGTH: 44
<212> TYPE: DNA
<213> ORGANISM: Rattus norvegicus
<220> FEATURE:
<221> NAME/KEY: misc_feature
<223> OTHER INFORMATION: Il2rg partial sequence around ZFN target

<400> SEQUENCE: 1
ccgaccaacc tcactatgca ctataggtat gagaaggggg aggg            44

<210> SEQ ID NO 2
<211> LENGTH: 15
<212> TYPE: DNA
<213> ORGANISM: Rattus norvegicus
<220> FEATURE:
<221> NAME/KEY: misc_feature
<223> OTHER INFORMATION: Il2rg ZFN left target sequence

<400> SEQUENCE: 2
gcatagtgag gttgg                                             15

<210> SEQ ID NO 3
<211> LENGTH: 15
<212> TYPE: DNA
<213> ORGANISM: Rattus norvegicus
<220> FEATURE:
<221> NAME/KEY: misc_feature
<223> OTHER INFORMATION: Il2rg ZFN right target sequence

<400> SEQUENCE: 3
ggtatgagaa ggggg                                             15

<210> SEQ ID NO 4
<211> LENGTH: 62
<212> TYPE: DNA
<213> ORGANISM: Rattus norvegicus
<220> FEATURE:
<221> NAME/KEY: misc_feature
<223> OTHER INFORMATION: Il2rg partial sequence around TALEN target

<400> SEQUENCE: 4
cccctcccag aggttcaatg ctttgtgttc aatgtcgagt atatgaattg cacttggaat   60
ag                                                                 62

<210> SEQ ID NO 5
<211> LENGTH: 18
<212> TYPE: DNA
<213> ORGANISM: Rattus norvegicus
<220> FEATURE:
<221> NAME/KEY: misc_feature
<223> OTHER INFORMATION: Il2rg TALEN left target sequence

<400> SEQUENCE: 5
```

```
tcccagaggt tcaatgct                                                    18

<210> SEQ ID NO 6
<211> LENGTH: 21
<212> TYPE: DNA
<213> ORGANISM: Rattus norvegicus
<220> FEATURE:
<221> NAME/KEY: misc_feature
<223> OTHER INFORMATION: Il2rg TALEN right target sequence

<400> SEQUENCE: 6
tccaagtgca attcatatac t                                                21

<210> SEQ ID NO 7
<211> LENGTH: 20
<212> TYPE: DNA
<213> ORGANISM: Rattus norvegicus
<220> FEATURE:
<221> NAME/KEY: misc_feature
<223> OTHER INFORMATION: CRISPR Guide RNA target sequence on Thy gene

<400> SEQUENCE: 7
tttccaggat tatgtaatag                                                  20

<210> SEQ ID NO 8
<211> LENGTH: 80
<212> TYPE: RNA
<213> ORGANISM: Artificial
<220> FEATURE:
<223> OTHER INFORMATION: crRNA:tracrRNA
<220> FEATURE:
<221> NAME/KEY: misc_feature
<223> OTHER INFORMATION: 3'end of CRISPR Guide RNA

<400> SEQUENCE: 8
guuuuagagc uagaaauagc aaguuaaaau aaggcuaguc cguuaucaac uugaaaaagu       60
ggcaccgagu cggugcuuuu                                                  80
```